(12) United States Patent
Butler

(10) Patent No.: US 6,234,030 B1
(45) Date of Patent: May 22, 2001

(54) MULTIPHASE METERING METHOD FOR MULTIPHASE FLOW

(75) Inventor: Bryan V. Butler, Garrison, TX (US)

(73) Assignee: Rosewood Equipment Company, Plano, TX (US)

( * ) Notice: Subject to any disclaimer, the term of this patent is extended or adjusted under 35 U.S.C. 154(b) by 0 days.

(21) Appl. No.: 09/143,035

(22) Filed: Aug. 28, 1998

(51) Int. Cl.[7] .............. G01F 1/74; G01F 15/08; G01F 7/00; G01N 33/22

(52) U.S. Cl. .......... 73/861.04; 73/195; 73/200; 73/61.44

(58) Field of Search .............. 73/861.04, 195, 73/197, 196, 198, 200, 61.41, 61.43, 61.44

(56) References Cited

U.S. PATENT DOCUMENTS

| | | | |
|---|---|---|---|
| 4,055,480 | 10/1977 | Smith et al. | 208/11 |
| 4,087,261 | 5/1978 | Hays | 55/41 |
| 4,144,754 | 3/1979 | Pitts, Jr. et al. | 73/205 D |
| 4,200,789 | 4/1980 | Arnold et al. | 250/270 |
| 4,210,015 | 7/1980 | Euzen et al. | 73/61.1 R |
| 4,215,567 | 8/1980 | Vlcek | 73/61.1 R |
| 4,282,760 | 8/1981 | Pitts, Jr. et al. | 73/861.02 |
| 4,292,011 | 9/1981 | Erickson | 417/53 |
| 4,294,695 | 10/1981 | Smith et al. | 210/173 |
| 4,396,508 | 8/1983 | Broughton | 210/187 |
| 4,403,911 | 9/1983 | Possell | 415/90 |
| 4,429,581 | 2/1984 | Furmaga | 73/861.04 |
| 4,431,534 | 2/1984 | Gordon | 210/110 |
| 4,441,361 | 4/1984 | Carlson et al. | 73/155 |
| 4,441,362 | 4/1984 | Carlson | 73/155 |
| 4,528,919 | 7/1985 | Harbolt et al. | 111/7 |
| 4,604,902 | 8/1986 | Sabin et al. | 73/861.04 |
| 4,646,273 | 2/1987 | Carlson et al. | 367/32 |
| 4,660,414 | 4/1987 | Hatton et al. | 73/61.1 R |
| 4,705,114 | 11/1987 | Schroeder et al. | 166/357 |
| 4,760,742 | 8/1988 | Hatton | 73/861.04 |
| 4,776,210 | 10/1988 | Baillie et al. | 73/61.1 R |
| 4,793,418 | 12/1988 | Wheeler et al. | 166/357 |
| 4,800,921 | 1/1989 | Greebe | 137/561 |
| 4,802,361 | 2/1989 | Bussian et al. | 73/61.1 R |
| 4,813,270 | 3/1989 | Baillie | 73/61 R |
| 4,822,484 | 4/1989 | Prendergast et al. | 210/96.1 |
| 4,824,614 | 4/1989 | Jones | 261/76 |
| 4,852,395 | 8/1989 | Kolpak | 73/61.1 R |
| 4,881,412 | 11/1989 | Northedge | 73/861.04 |
| 4,884,457 | 12/1989 | Hatton | 73/861.04 |
| 4,924,695 | 5/1990 | Kolpak | 73/61.1 R |
| 4,974,446 | 12/1990 | Vigneaux | 73/155 |
| 4,974,452 | 12/1990 | Hunt et al. | 73/861.64 |
| 4,979,880 | 12/1990 | Delaittre | 417/406 |
| 5,020,359 | 6/1991 | Castel | 73/61 R |
| 5,025,160 | 6/1991 | Watt | 250/356.1 |
| 5,033,288 | 7/1991 | Castel | 73/61.1 R |
| 5,036,710 | 8/1991 | King | 73/861.04 |
| 5,047,632 | 9/1991 | Hunt | 250/302 |
| 5,049,823 | 9/1991 | Castel et al. | 324/640 |
| 5,070,725 | * 12/1991 | Cox et al. | 73/61.44 |
| 5,083,452 | 1/1992 | Hope | 73/61 R |
| 5,095,983 | 3/1992 | Magnani | 166/250 |
| 5,127,272 | 7/1992 | Dean et al. | 73/861.04 |
| 5,149,344 | 9/1992 | Macy | 55/167 |
| 5,150,061 | 9/1992 | Castel et al. | 324/640 |
| 5,156,537 | 10/1992 | Massinon | 417/536 |

(List continued on next page.)

Primary Examiner—Benjamin H. Fuller
Assistant Examiner—Jagdish Patel
(74) Attorney, Agent, or Firm—Standley & Gilcrest LLP

(57) ABSTRACT

The present invention includes a method for multiphase metering of multiphase flow. the method begins with reducing gas volume to about 20% or less, then pumping the flow stream through two meters, a cut meter and a mass flow meter, arranged in series. Computations may be made on the flow stream to determine net oil rate, water cut, and gas fraction in the flow stream.

18 Claims, 13 Drawing Sheets

U.S. PATENT DOCUMENTS

| | | | |
|---|---|---|---|
| 5,173,195 | 12/1992 | Wright et al. | 210/802 |
| 5,195,380 | 3/1993 | Hatton et al. | 73/861.04 |
| 5,203,211 | 4/1993 | Jung | 73/861.04 |
| 5,205,310 * | 4/1993 | Kolpak et al. | 137/2 |
| 5,209,765 | 5/1993 | Kolpak et al. | 55/168 |
| 5,211,842 * | 5/1993 | Tuss et al. | 73/861.04 |
| 5,214,284 | 5/1993 | Tokunaga et al. | 250/309 |
| 5,218,840 | 6/1993 | Kolpak | 73/61.44 |
| 5,224,372 | 7/1993 | Kolpak | 73/19.03 |
| 5,226,482 | 7/1993 | Giannesini et al. | 166/353 |
| 5,251,488 | 10/1993 | Haberman et al. | 73/861.04 |
| 5,254,292 | 10/1993 | Gabryelczyk et al. | 261/76 |
| 5,259,239 * | 11/1993 | Gaisford | 73/61.44 |
| 5,290,151 | 3/1994 | Orlando | 417/54 |
| 5,306,911 | 4/1994 | Hunt | 250/302 |
| 5,353,627 | 10/1994 | Diatschenko et al. | 73/19.03 |
| 5,353,646 | 10/1994 | Kolpak | 73/861.04 |
| 5,375,618 | 12/1994 | Giannesini | 137/110 |
| 5,375,976 | 12/1994 | Arnaudeau | 415/199.5 |
| 5,377,714 | 1/1995 | Giannesini et al. | 137/2 |
| 5,390,547 | 2/1995 | Liu | 73/861.04 |
| 5,393,202 | 2/1995 | Levallois | 417/19 |
| 5,400,657 | 3/1995 | Kolpak et al. | 73/861.04 |
| 5,415,024 | 5/1995 | Proffitt et al. | 73/61.44 |
| 5,431,228 | 7/1995 | Weingarten et al. | 166/357 |
| 5,437,299 | 8/1995 | Kolpak | 137/1 |
| 5,447,370 | 9/1995 | Cessou | 366/167.1 |
| 5,456,120 | 10/1995 | Simonian | 73/861.04 |
| 5,461,930 * | 10/1995 | Farchi et al. | 73/861.04 |
| 5,483,171 | 1/1996 | Hatton et al. | 324/640 |
| 5,485,743 | 1/1996 | Taherian et al. | 73/61.44 |
| 5,526,684 | 6/1996 | Liu et al. | 73/200 |
| 5,531,112 | 7/1996 | Young et al. | 73/152 |
| 5,535,632 * | 7/1996 | Kolpak | 73/861.04 |
| 5,561,245 | 10/1996 | Georgi et al. | 73/152.02 |
| 5,575,615 | 11/1996 | Mohn | 415/74 |
| 5,575,625 | 11/1996 | Castel | 417/178 |
| 5,580,214 | 12/1996 | Mohn | 415/64 |
| 5,586,027 | 12/1996 | Carlson et al. | 364/422 |
| 5,591,922 | 1/1997 | Segeral et al. | 73/861.04 |
| 5,597,961 | 1/1997 | Marrelli | 73/861.04 |
| 5,608,170 | 3/1997 | Atkinson et al. | 73/861.04 |
| 5,631,413 | 5/1997 | Young et al. | 73/152.29 |
| 5,635,631 | 6/1997 | Yesudas et al. | 73/61.46 |
| 5,646,352 | 7/1997 | Joseph et al. | 73/756 |
| 5,654,502 * | 8/1997 | Dutton | 73/861.04 |
| 5,654,551 | 8/1997 | Watt et al. | 250/356.1 |
| 5,660,532 | 8/1997 | Castel | 417/342 |
| 5,660,617 | 8/1997 | Hatton | 95/254 |
| 5,661,237 | 8/1997 | Dussan | 73/152.18 |
| 5,661,248 | 8/1997 | Bernicot et al. | 73/861.04 |
| 5,680,899 | 10/1997 | Waid et al. | 166/250.01 |
| 5,698,791 | 12/1997 | Lemaire | 73/861.04 |
| 5,706,211 | 1/1998 | Beletic et al. | 364/514 R |
| 5,707,427 | 1/1998 | Stockman et al. | 95/260 |
| 5,710,717 | 1/1998 | Hong et al. | 364/510 |
| 5,711,338 | 1/1998 | Talon | 137/8 |
| 5,736,637 | 4/1998 | Evans et al. | 73/152.31 |
| 5,741,977 | 4/1998 | Agar et al. | 73/861.04 |
| 5,747,674 | 5/1998 | Moracchini et al. | 73/61.44 |
| 5,770,068 | 6/1998 | Jepson | 210/741 |
| 5,775,879 | 7/1998 | Durando | 417/45 |
| 5,777,278 | 7/1998 | Bednarczyk et al. | 181/102 |
| 5,792,962 | 8/1998 | Constant et al. | 73/861.04 |
| 5,793,216 | 8/1998 | Constant | 324/639 |
| 5,810,032 | 9/1998 | Hong et al. | 137/561 A |
| 6,032,539 * | 3/2000 | Liu et al. | 73/861.04 |
| 6,076,049 * | 6/2000 | Lievois et al. | 73/861.04 |

* cited by examiner

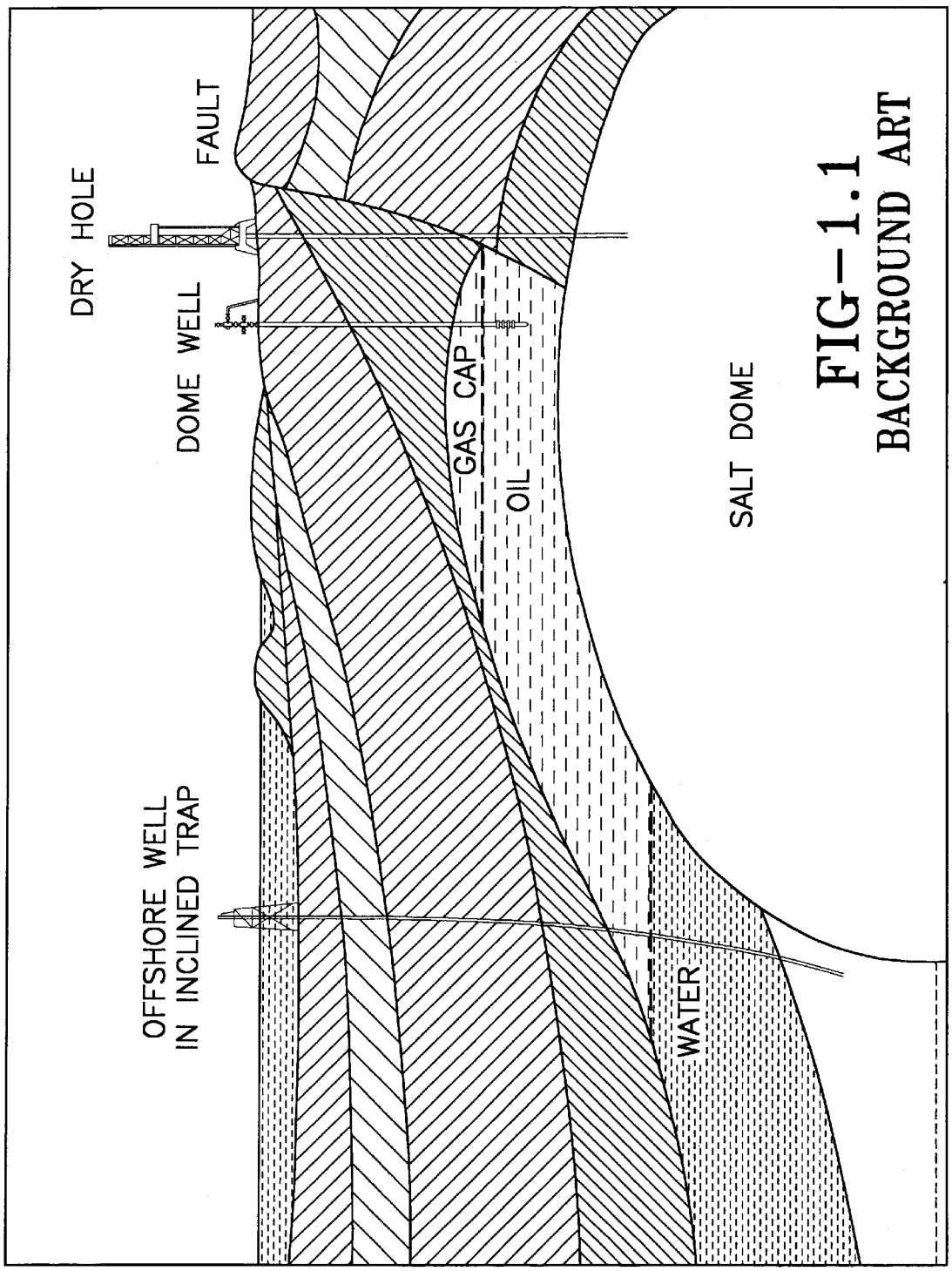
FIG-1.1
BACKGROUND ART

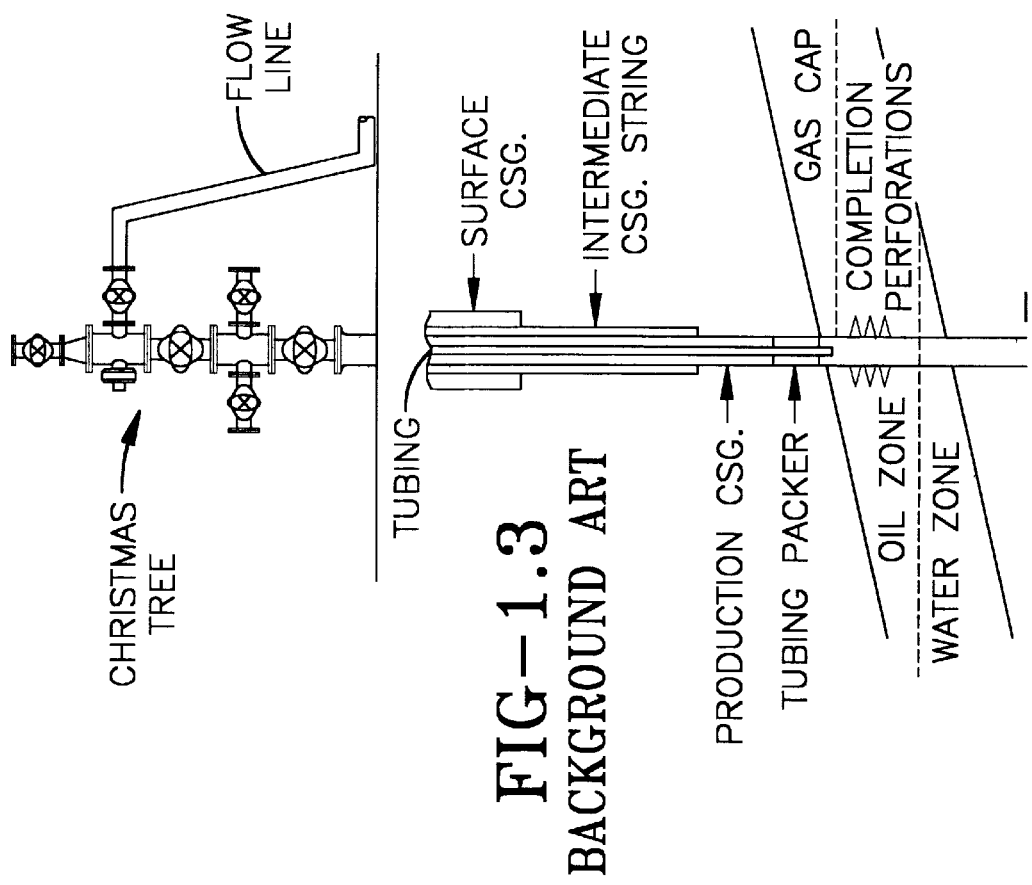
FIG-1.3
BACKGROUND ART
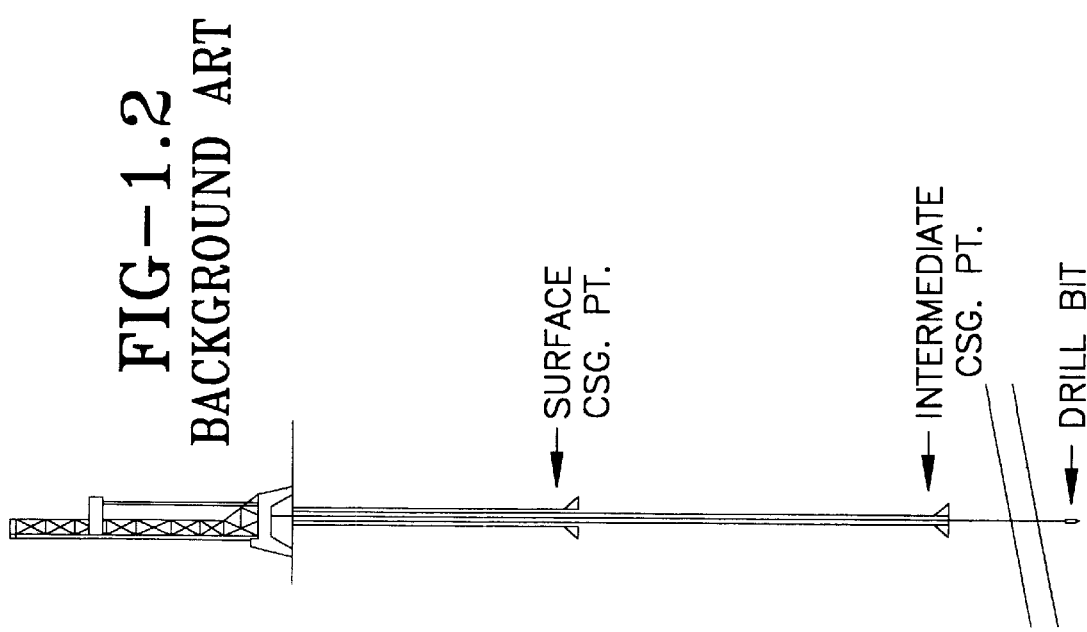
FIG-1.2
BACKGROUND ART

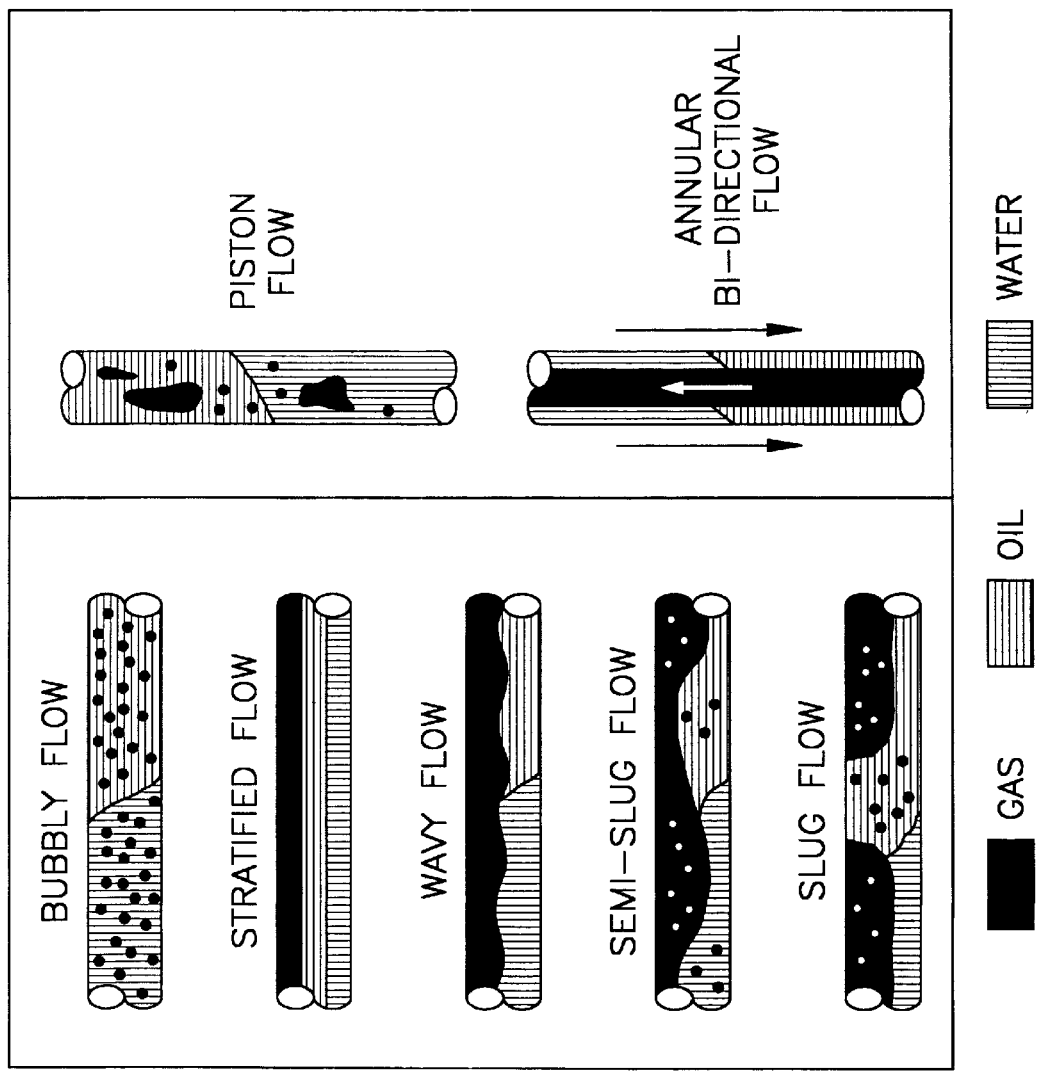
FIG-2.1
BACKGROUND ART

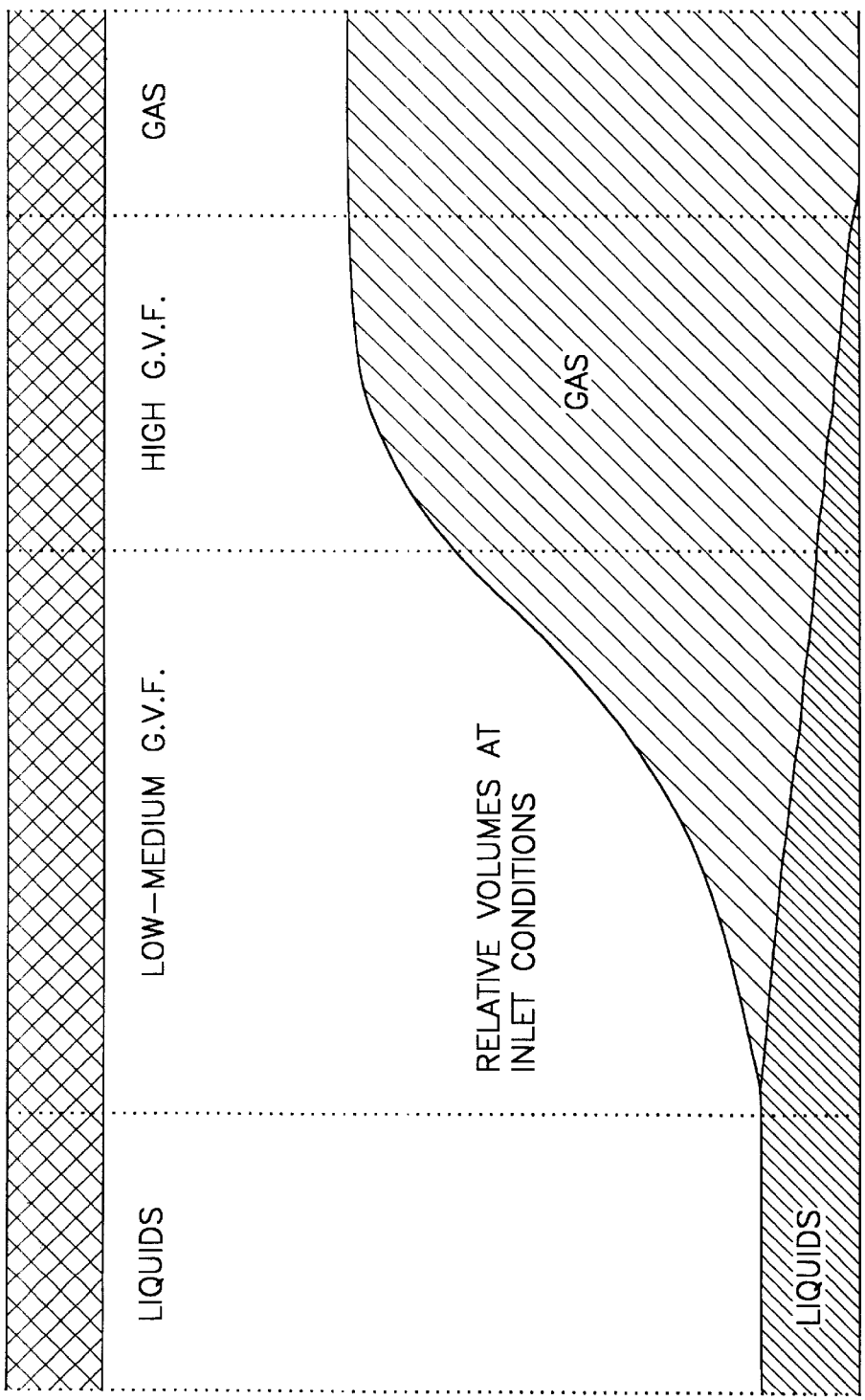
FIG-2.2
BACKGROUND ART

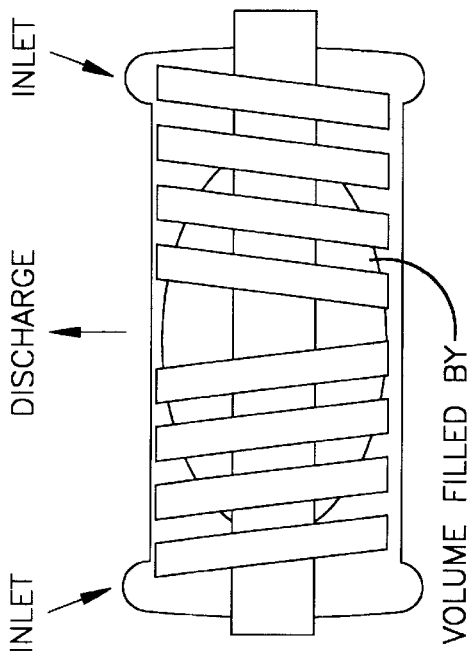
FIG-2.3A
BACKGROUND ART
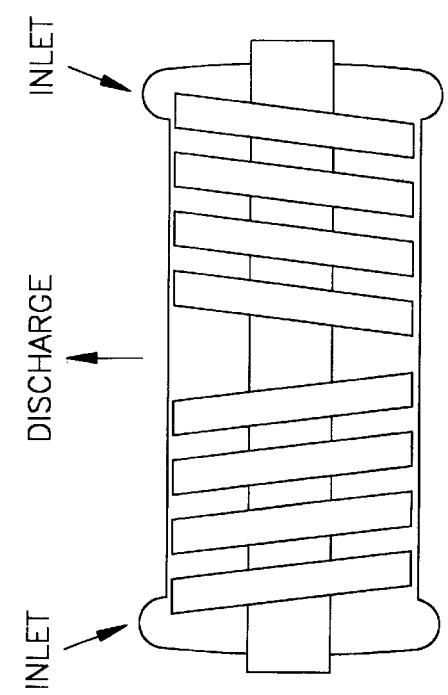
FIG-2.3B
BACKGROUND ART
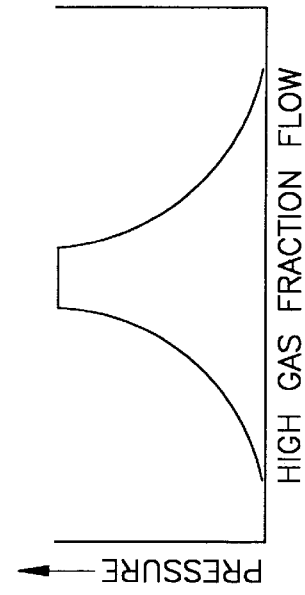
FIG-2.4A
BACKGROUND ART
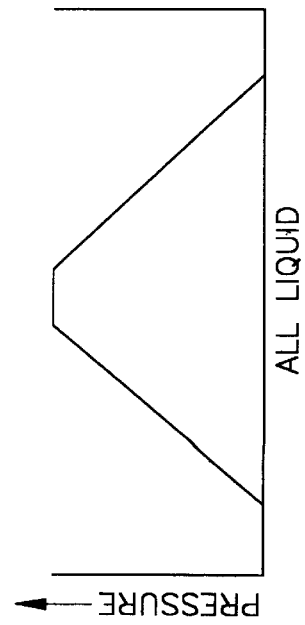
FIG-2.4B
BACKGROUND ART

MULTIPHASE CALCULATIONS FOR SIZING A METER OR PUMP

| COL. 1 | 2 | 3 | 4 | 5 | 6 | 7 | 8 | 9 | 10 | 11 | 12 |
|---|---|---|---|---|---|---|---|---|---|---|---|
| WELL OR LINE DESCRIPTION | OIL BOPD | WATER BWPD | LIQUIDS BPD | GAS MSCFPD | TP PSI | TEMP DEG F | TEST PRESS PSI | EQ. GAS MACFPD | EQ. GAS BPD | TOTAL BPD | GVF % |
| LION B-1 | 1760 | 0 | 1760 | 5629 | 880 | 200 | 500 | 208 | 37060 | 38820 | 95.5 |
| LION B-2 | 1835 | 67 | 1902 | 4249 | 755 | 200 | 500 | 157 | 27974 | 29876 | 93.6 |
| LION B-3 | 3588 | 0 | 3588 | 9679 | 1265 | 200 | 500 | 358 | 63724 | 67312 | 94.7 |
| LION B-4 | 1407 | 117 | 1524 | 2657 | 790 | 200 | 500 | 98 | 17493 | 19017 | 92.0 |
| LION B-5 | 1082 | 27 | 1109 | 3852 | 1475 | 200 | 500 | 142 | 25361 | 26470 | 95.8 |
| LION B-6 | 36 | 0 | 36 | 400 | 560 | 200 | 500 | 15 | 2634 | 2670 | 98.7 |
| TOTALS: | 9708 | 211 | 9919 | 26466 | | | | 978 | 174246 | 184165 | 94.6 |

MULTIPHASE MEASUREMENT NOTES:

1. Data in Columns 1–6 supplied by customer, Columns 7 and 8 assumed from conversations, 9–12 calculated to arrive at actual volumetric flows.
2. Italicized Data is from the Customer.
3. Column 9 is Column 5 x {(Col. 6 + 460)/520} x {15/(Col. 8 + 15)}
4. Column 10 is Column 9/5.615 x 1000
5. Column 11 is Col. 10 + Col. 4
6. Column 12 is Col. 10/Col. 11 x 100

FIG-2.5

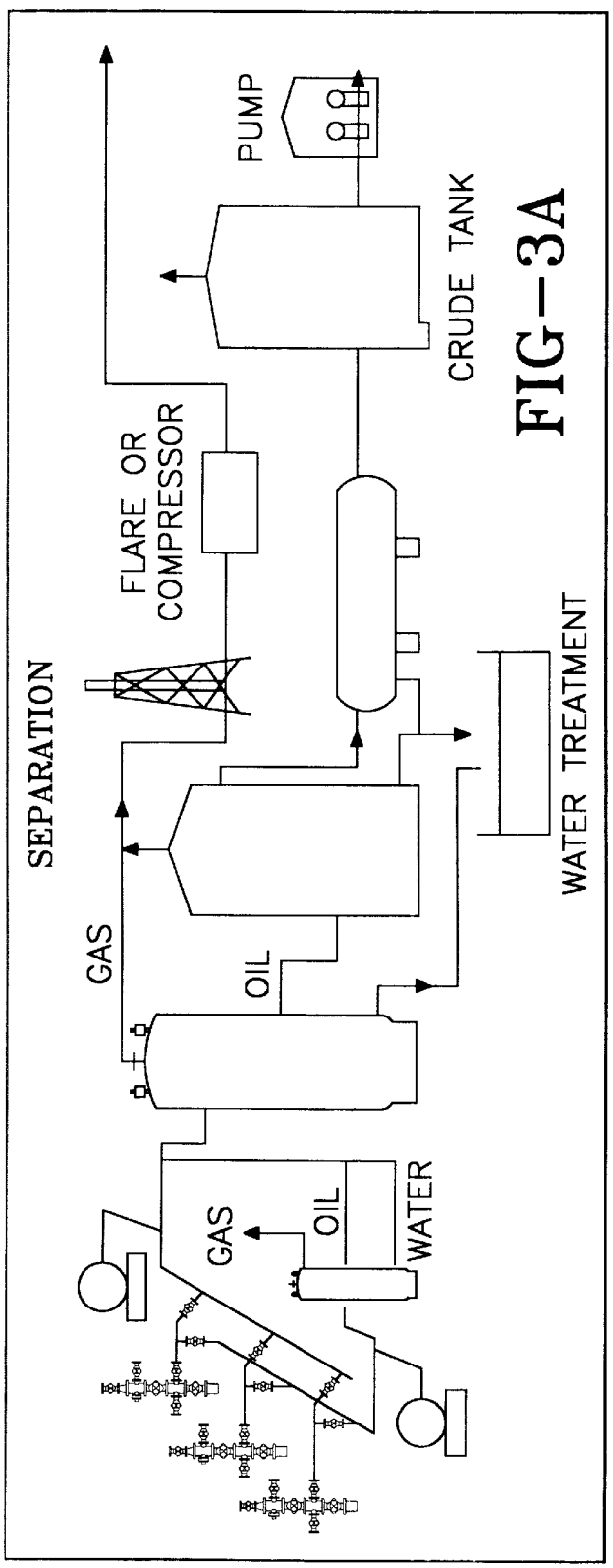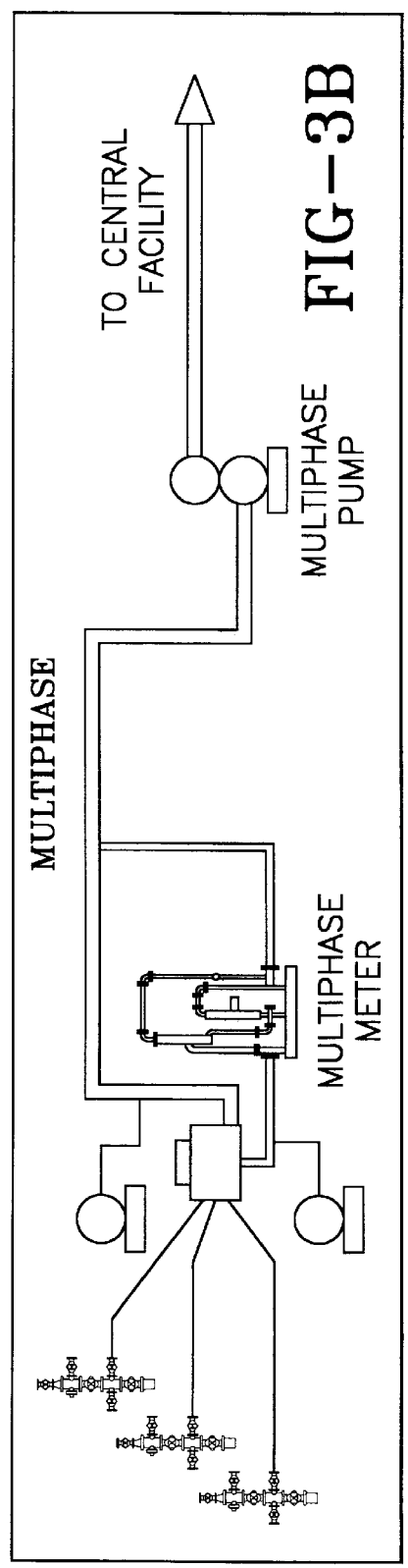

MULTIPHASE METERING METHOD FOR MULTIPHASE FLOW

BACKGROUND AND SUMMARY OF THE INVENTION

The present invention relates generally to multiphase metering and multiphase flow, and more particularly, to a method for handling oil, gas and water flow during petroleum production.

The word Petroleum means "rock oil" or "oil from rocks". Oil and gas begins to form as part of a biogenic decay process which happens under a variety of geologic circumstances that usually involve anaerobic conditions. Plankton, or other higher forms of life die and are deposited in marine basins, to be covered by the soft muds that are formed there. These are subsequently overlain with other types of deposits, sequentially building up, much in the manner observed today near the outlets of the Texas rivers where they meet the waters of the Gulf.

As these source beds compact over geologic time, the ancient sea water along with the oil and gas move into overlaying formations that are more porous, such as sandstones. If hard limestones have formed, and subsequently have fractured, these fluids can also find their way into these fissures and cracks and into the vugular cavities that may be present. Eventually these fluids collect and redistribute themselves within these porous formations, with water tending to collect near the base and the gas moving upward toward the cap. Natural seals formed by the base rock and cap rocks (dense limestones or shales usually, sometimes salt plugs), serve to trap these fluids, and may allow pressures to build up as more gas forms, or as the reservoir rocks themselves compress from additional weight of the overmass. (See FIG. 1.1)

Petroleum production starts when man drills into one of these porous sections and encounters sufficient oil and or gas under conditions that will permit commercial exploitation. Tests are performed on the exploratory wells that encounter the formation, and logs are run to help evaluate the find.

"Development" wells are next. These wells are drilled from land sites or from platforms and usually are started with a large diameter hole, into which 20 inch or 16 inch casing is run and cemented. The cementing process is used to bond the casing to the rock and to form a seal. During drilling the blow out preventors (BOPs) are bolted and sealed to the top assembly of this casing system, known as the wellhead. The wellhead together with the surface string forms the support for the subsequent casing strings that will be set in the well as it is drilled to greater depths.

Each intermediate casing string (e.g.; 13 ⅜ths, 9 ⅝ths) is hung from the wellhead (according to the drilling program of the well), where it is sealed, and then cemented through the shoe joint on the bottom to seal off the string. (Refer to FIG. 1.2.) A smaller bit is then used to drill out through the shoe into deeper zones, and is followed by the next casing string, etc. The driller logs (and may take samples) in the open hole of each new sequence before setting casing, using a logging service. Mud logs (a continuous report on drilling progress based on examination of the mud and cuttings circulating out of the hole during drilling) are often kept. The production string of casing is the final string run, and when it is in place and cemented, the well is ready for completion.

The term "completion" encompasses a number of methods that determine how the well will communicate with the producing intervals is penetrated. This can range from "barefoot" or open hole completions, to hung liners, to perforated casing, and nowadays may include drilling one or more laterals into the formation for horizontal completions. The basic idea is to maximize the capability of the well to produce hydrocarbons without the side effects of producing water and sand, and to minimize the production of the gas cap (gas already present in the reservoir).

Included in the completion scheme is the tubing string and any downhole pumping or gas injection methods. Tubing is run into the well through the production string of casing, and generally a packoff is set above the producing interval. If the well has enough pressure, it can produce by flowing through the tubing. The annulus between the tubing and the casing is usually dry or may be filled with a fluid, such as water. If it cannot flow, then some form of down hole pumping or gas injection can be used to assist production.

The tubing string is suspended from the tubing hanger (or tubing head) located above the wellhead and bolted and sealed to it. The BOP is removed and replaced by the Christmas tree, which is the combination of valves assembled together to provide surface shut off control to the tubing, to the casing annulus, and to the flow line connected to the tree. Gages are included in this assembly to indicate the pressure and temperature conditions of the flow coming through the tree and to monitor the casing annulus pressure. (Refer to FIG. 1.3.)

The production from the tree is sent through a choke into a flow line, which is connected to a gathering manifold, often called the production manifold, well battery, trap farm, etc. (local jargon may prevail here). It enters this manifold through a shut off valve, and has an alternate flow line connected through another valve to a test manifold. This means the flow from the well can either go directly into the production processing equipment, or flow to this equipment via a testing device. See FIG. 1.4 that depicts a well testing schematic at a gathering center.

The most common testing device is the test separator, a device that is operated to more or less mimic the pressure and temperature conditions of the production separator. Its purpose is to provide information about the productivity of an individual well and to record the amount of oil, gas, and water that well is extracting from the reservoir. Other testing schemes include strapping tanks (calibrated tanks) and sampling systems for water cut draw offs. The newest type of well tester is the multiphase flow meter.

This test data (after allocation as explained below) is maintained and accumulated for each well over the life of the well. It is also reported (usually a legal requirement) on a monthly basis to a governmental agency. The production quantities and overall trends are used by reservoir engineers and production geologists to identify new prospects for development or to design enhanced recovery programs (such as waterflooding). They are also interested in short term, daily or hourly test data to evaluate the productivity of the formation at the well bore interface. This production data may be augmented from time to time with pressure data taken from the well. Of particular interest is a pressure build-up vs time survey taken by shutting in the well with a pressure "bomb" (i.e., recorder) hung in the well. It is a very unpopular practice from the viewpoint of production people as it reduces production income and has the risk that the well may not come back fully to its pre-test productivity. With the advent of multiphase metering is offered a new approach where a flowing well is sequentially reduced in its production (choked back) in four steps. The key is to know when the production has stabilized after each step has been made (which is provided by the minute to minute data of the multiphase meter). In this way, without shutting in the well, the same type of data needed for the reservoir engineer to calculate permeability, well bore damage (the "skin effect"), boundary proximity's, and other information important to reservoir management and workover planning can be obtained.

The production engineers are also interested in the well's production data, but more from the standpoint of evaluating the mechanical condition of the well, and the efficiency of the operation of the equipment used for production (the type of pump, the condition of the packoffs, size of tubing, monitoring for paraffin deposits and build up, tubing leaks, surging, etc.). The overall production data will determine if the well is economic (i.e., paying for itself) whereas the trending data (day-by-day from separators; minute-by-minute from multiphase meters) is used to evaluate the effects of changes that have been made to the operation (optimization).

Once tested, the flow from an individual well can be combined with the flow from other wells. Here the decision may be to try to flow to the processing facility using the energy from the well, or it may be decided to boost the pressure. Since the flow is still multiphase, the decision to boost will require a multiphase pump, which represents using new technology. However, making this decision can result in improved and prolonged well production by lowering the back pressure on the well, and may avoid construction and operation of separation facilities near the wells. Offsetting these cost and income benefits may be the additional cost of pumping.

The production separator receives all the combined flow from the individual wells, and is used to separate the oil, gas, and water. Frequently conditions are such that this process works in stages in order to get "all" of the gas to "break out". This produced gas may then be measured, compressed and put into a pipeline for transport to a treatment plant and on to market. Alternately, it may be flared (burned off) locally. If, as is commonly the case, the remaining water and oil phases are intermingled as an emulsion, additional treatment is often required to get these to separate, and to coalesce into two liquids, allowing each to be decanted off. Sometimes sand and silt are produced in quantities that require special cleaning and disposal at this point. Process equipment used in production treatment includes "wash tanks, heater-treaters, centrifuges, and jetting equipment, and settling tanks and lagoons, with baffles, dispargers, skimmers, filters, and other devices, along with pumps, recirculation lines, and associated probes and monitors, etc. Occasionally (e.g., in the country of Peru) the crude oil must also be desalted before it is ready for shipment and a desalter is used after the heater treater to pull out any heavy ions, chlorides, and potassium from the oil that the refinery downstream will find unfriendly.

Once this treatment process is completed, the processed, "dead" (degassed) crude is stored in the stock tank(s), ready for shipment by truck or pipeline. Normally this crude is measured as it leaves the tank, or the tank levels themselves are strapped. If this point is a custody transfer point, a lease automatic custody transfer (LACT) unit may be employed, using highly accurate flow meters (precision of 0.0002:1) to measure the oil.

This oil shipment data is reported back to the production operating group, where it is adjusted to reflect the daily rate produced from all of the wells. Normally there is a difference due to additional shrinkage of the oil (outgassing and some temperature effects, etc.). After these are accounted for, the remaining difference is assumed due to the error in measuring the individual wells through the test separators, and this is allocated back to the individual well test data, usually by prorating based on the number of days produced that month, and the relative amounts of crude produced. This error can be anywhere between 5 to 50% (in some cases 100%!), depending on the operation of the test separator. In most of the cases, the test separator will show too much oil compared to the LACT unit's figures.

The significance of these practices is that the allocated, adjusted figures are the ones used by the oil company to record well performance and to evaluate the condition of the well. The pervasive effect of misallocation is indicated by the poor performance of the workover programs which are often undertaken to improve the performance of a well, and following the workover, very little change results. In many cases this means that the wrong well got the treatment. It can also result in a wrong decision regarding the position of the next development well, or the location of a new injector in a waterflood.

Historically oil has been the principle fluid of financial interest to the producer. It is sold from the storage tank or the pipeline at "stock tank conditions", which are adjusted to Standard Conditions (STP=Standard Temperature and Pressure). Standard Temperature is 60 deg. F. (520 deg. Rankine), and Standard Pressure is 14.7 psia (1 Atmosphere). These are the conditions that define the standard bulk volume of a "blue barrel of oil", or bbl. (the "blue" refers to the common color of a 42 gallon barrel of oil as sold by the Standard Oil Company and which became the common commercial standard in the USA.) These conditions also defined the standard volume of gas, commonly stated as a Standard Cubic Foot (scf). Since these quantities commonly occur in the thousands or millions, the industry will usually express gas volumes in units of thousand cubic feet (MCF) or million cubic feet (MMCF). Unless stated otherwise, the volumes are taken to be at standard conditions.

If an oil well produced a quantity of oil and gas and water from the reservoir, the quantity of oil obtained at the stock tank was measured as well as the quantity of gas. This volume of gas was usually referenced to the oil that was produced with it, by using the ratio of scf/bbl, also referred to as the GOR (Gas Oil Ratio). Any water and basic sediment (BS&W) produced with the oil was also measured and expressed as a percentage of the total liquid (oil+water). This value is referred to as the water cut. The term "net oil" or "net" refers to the oil production after water has been subtracted. The combined oil and water production is commonly called the total production, or gross production, with the gas expressed either as a total volume (MCF) or as the GOR. Sometimes the GOR will be shown as the GLR, or gas-liquid ratio, in which case one adds the water production to the oil production before multiplying the total liquid times the GLR to get the quantity of gas being produced.

There is a specific relationship established, usually through laboratory analysis, between the volume occupied by a barrel of oil under stock tank conditions and under reservoir conditions. Three factors come into play: the temperature, pressure, and the solubility of the gas. Oil in the stock tank has lock most of the gas that was originally in solution in the oil in the reservoir during the journey is made through the reservoir to the well, up the tubing, through the flow line, and into the separator system before being collected in the stock tank. It also traveled with the non-associated gas (gas already in the reservoir as gas). These factors, along with pressure reductions and temperature changes allowed the oil to "shrink" from its reservoir volume to its stabilized volume under stock tank conditions, where it is referred to as "dead" oil. The ratio of the volume occupied in the reservoir compared to the volume in the tank is represented by a B factor, Bulk Volume factor commonly ranges from 1.05 for lower pressure reservoirs on up to 1.35 for higher pressured reservoirs containing oil in which gas is readily soluble. (It simply means that a stock tank bbl of oil, when recombined with the gas it had in solution would occupy 1.35 barrels of reservoir pore space.)

Therefore, whenever volumes are measured for oil and gas and water, it is important to know how to relate these values to standard conditions so that the STP values can be sued by the various engineering disciplines to calculate what new volumes are to be expected when converting to reservoir or to pipeline conditions. The industry refers to this relationship as "PVT" data (Pressure, Volume, Temperature), and it is available from specific laboratory analyses of the hydrocarbon of each formation, or can be closely estimated using the standard tables by Standing.

Multiphase Flow

Multiphase Flow contains a mixture of gas, oil and water. It appears in several forms, commonly called flow regimes, most of which are characterized in FIG. 2.1. During movement of these fluids through a pipeline one or all of these forms may be present.

Measuring and pumping of multiphase fluids occurs under a wide variety of temperatures and pressures, accordingly, people in this discipline should become familiar with the relationships and terminology mentioned in the foregoing section. Fortunately the pressures and temperatures commonly encountered at the surface are relatively low when compared to conditions in a reservoir, hence one of the factors mentioned, the solubility of gas, has only minor effect and can usually be ignored for most application purposes.

Crude oils differ in their chemical makeup, and will exhibit a variety of behavior with respect to changes in temperature and pressure. These changes will affect the viscosity gas solubility, emulsion formation, emulsion stability, foaming, asphaltene deposition, and numerous other characteristics. The chemistry of the water phase can also be highly variable, depending on the dissolved salts and gases found therein. For these reasons it has been difficult to predict with a survey just how one crude will behave in a flow line compared to another, and then when effect external influences such as temperature, pressure, pipe wall friction, etc., will have. Added to this complexity is the effect of varying amounts of compressible gas and you have the somewhat unpredictable world of multiphase flow.

Researches observing multiphase flow through transparent wall piping also notice that as the gas volume fractions increase, the reduced volumes of liquids are tossed about in the flow, mostly moving forward in slugs, but also draining down the sides of the pipe after the slug passes. In vertical pipe sections this liquid can flow downward while the gas with entrained liquids are being transported upward. This type of bi-directional flow occurs naturally in wells, causing them to periodically surge with liquid flow followed by periods of gas flows that vary greatly in velocity and pressure (Old Faithful geyser is a natural example). When bi-directional flow occurs in a multiphase meter it can greatly increase its error and is a type of flow to be avoided.

Once at the surface, the formation of liquid slugs will often occur in low spots in the line, with the gas flowing on by (slip flow) to form larger and larger gas slugs. The larger the line diameter and the greater the average volume of gas present relative the total volume of flow, the more pronounced this effect. For this reason the Gas Volume Factor (GVF) is often computed in multiphase flow applications as an indicator of how developed the gas slugs might be. Unfortunately, it is sometimes forgotten to look at the rest of the situation relative to line size and its geometry as it approaches the meter or pump. Geometery can easily have an effect as pronounced as GVF on slug formation, size and duration.

Temperature can also affect slug formation. If liquids with viscosity behavior sensitive to temperature levels (e.g., heavy crudes) collect in low spots in a flow line during the evening when temperatures are dropping, they may tend to get "stuck" there, building up more than they would if the temperature were higher. Gas will build up pressure and finally push on by, creating much longer and larger gas slugs downstreams. When finally the liquid slug moves, it will move as a large plug, arriving at the meter or pump in a much different fashion than experienced during the daylight hours.

Conditions leading to multiphase flow develop whenever the flow line pressure and temperature combine at levels that allow gas to form. In the reservoir this combination of pressure and temperature is referred to as the "bubble point" or "bp." Reservoirs that contain oil in situ above the bp will, generally, start to flow oil into a new well as a liquid, but as soon the pressure is reduced in the tubing or in the surface flow line, gas will come out of solution and form bubbles. As additional oil flows into the well from further back in the reservoir, these gas bubbles will also flow, increasing the ratio of gas produced per barrel of oil (the GOR). As time goes by the GOR rises further and further until the reservoir gas pressure is exhausted.

At the surface the flow line pressures are usually much lower and the gas expands substantially, occupying the major volume in the flowline. The ratio of this gas volume to the total volume is the Gas Volume Factor, and is often referenced in calculations related to multiphase flow. FIG. 2.2 shows some parametric relationships developed for the GVF in a flowline versus the GOR of the oil production for normal low pressure surface lines. It can be appreciated from this presentation that, in general, GVF's above 0.85 (85%) can be expected for GOR's in excess of 180 to 250 scf/bbl. and that since these GOR values are often found early in the productive life of the reservoir, the majority of multiphase flow situations will be at GVF values greater than 85%.

Multiphase Pumping

Multiphase Pumping consists of taking incoming multiphase flow and discharging continuously against a higher pressure regime. Since slug flows will be the norm, the pumps must be able to manage flow regimes ranging from 100% gas to 100% liquids. At times the flow may contain sand in varying proportions, In some production environments the liquid viscosities may be varying during the pumping cycle. The most successful types of pumps for this service have been the twin screw pumps. (See FIG. 2.3a and FIG. 2.3b for examples of such pumps.) Incoming fluids flow into two inlet chambers located at either end of the twin screw shafts. One shaft is connected to a prime mover, usually an electric motor. The other shaft is rotated in the opposite direction through a gear train. The two screws intermesh to form a seal that forces the trapped volumes to move axially toward the discharge point.

Pressure is generated as a reaction to pushing this fluid volume into the discharge chamber and is not generated by the pump itself. It should also be noted that a constant fluid volume is advanced as the screw is turned, so volumetric output is a function of the screw RPM for any given model of pump.

Because the intake chambers are at either end, they receive equally the slug flow from the incoming line so there is negligible effect on the shaft bearings (pressure balanced). Likewise, the discharge pressures act in both directions along the centerline of each shaft.

However as the volumes move toward the higher pressure region, there is a pressure distribution between the two shaft that results in an unbalanced transverse force on each shaft, tending to deflect them apart. These forces are resisted structurally by using short shaft lengths, and by using thick diameters. In one known design this is done with a single piece forging for the shaft; in another version the shafts are keyed to sleeves that are cut with the threads.

FIG. 2.4a is a simplified model of the pressure distribution along the screw shafts created by pumping an incompressible fluid. The increase in pressure is essentially linear between the low pressure chamber and the discharge chamber. Pressure stability during pumping is maintained via liquid "seals" in the clearances that exist at the edge of each tread. Normally these clearances are maintained at approximately 0.01 inches by careful machining and by the stiff design of the rotors. In this mode and particularly when the GVF and the delta pressure are low, the pump is capable of relatively high pumping efficiencies. In general, if pumping at relatively low delta p and essentially 100% liquids, these efficiencies will be on the order of 80%, with the better efficiencies obtained with higher viscosity fluids.

However, as the differential pressure increases, so does the slip flow rate across the liquid seal surfaces, causing a drop in the volumetric efficiency. The drop is inversely proportional to the viscosity of the liquid.

In FIG. 2.4b the volumetric distribution of the pumped fluid is shown when a substantial volume is in the gas phase. Assuming for the moment isothermal compression and a multiphase flow of 85% gas volume into a pump boosting from 30 psig to 400 psi, the 85% volumetric portion would be reduced to about 3%, and the total volume exiting the pump would be 18% of the original volume. Within the screw compartments as the fluid moves toward higher pressure the compressible portion is reducing more and more rapidly (hyperbolic function) until it is practically at the 18% value in order to meet the discharge pressure conditions.

To fill in this volume the pump receives fluid (mainly gas) from the discharge area. Since the delta p at the first stage is relatively small, the tendency to slip flow back into the inlet chamber would normally be reduced, however, because the gas can move across this area fairly easily, the volumetric slip flow is actually more than in the case of the 100% liquid pumping condition with a higher delta p.

Helping to offset this effect somewhat is the polytropic expansion of the gas due to the heat of compression, which fills some of the void created by the pressure increases and reduces the back flow requirements. However another effect that can overcome this advantage is flashing of the light ends of the crude in the inlet chamber and along the way, which increases the volume to be handled by the pump. Flashing can also occur when the liquids are pumped back as recirculated liquid into the seals and into the pumping chamber.

The net effect is that the volumetric efficiency of a pump handling high GVF in combination with a crude containing light components can drop to half of its rated throughput efficiency. Since this is happening when the gas volumes are already high and are likely to be increasing over time, maintaining pump capacity can become critical in such applications.

The pump shafts employ rotating seals that, if operated dry, can generate excessive heat, damaging the seals. Liquid must be constantly circulated to remove this heat and to provide lubricity. This same liquid is pushed through a throttle bushing, (or, alternatively, injected directly) into the inlet to coat the rotors so that the liquid seal present at the rotor clearances is maintained. When this is partially lost, the pump will lose even more pumping capacity. If this seal is totally broken down, the pump may gas lock, rotating without moving any volume.

For these reasons it is important that the pumping system be capable of supplying an adequate amount of lubricating and cooling circulation fluid. A rule of thumb for one known pump is to supply approximately 5 percent of the volume of the throughput flow. This 5% should be effective, that is, enter the pump as a liquid and remain in that phase. If most of it flashes it will not only sharply reduce throughput, but add to the dryness in the pump and will not be effective in heat removal. If the liquid is brought into recirculation by trapping it from the flow stream and the crude is a heavy crude one must also be careful of plugging the recirculation lines due to high viscosities, or due to formation of asphaltenes in the lines. If additional (outside) liquid sources are needed it is important to look at the effect this liquid (such as water-glycol) will have on emulsion formation downstream in the crude, and any other effect it might have if it leaks into the gear train. The gear train should also be lubricated, either through a sealed system, or with a system of lubricant make up.

The pump temperature should be monitored, and a suitable automatic shut down method provided to protect the pump from excessively high temperatures. It may also be important to monitor the recirculation liquid sources to warm of inadequate supply.

A suitable start up procedure and monitoring method should be included in the pumping system. An inlet filter or screen (course) should be included.

For proper pump sizing the inlet volume of all phases needs to be calculated. This means the gas volume must be known and converted to the volumes it will occupy under the pressure and temperature of the inlet conditions. If the gas volume factor under these conditions is appreciably high (>60%) the volumetric efficiency must be reduced for the pump accordingly. A sample of how to organize this data and calculate it is attached in FIG. 2.5.

Considering now ultra-high gas volume factors, it was noted in Section 1 that production from mature reservoirs will often result in GVFs above 90%. While the multiphase pump can be made to operate under these conditions, there are two downside effects:

1. Since the pump must be sized for inlet conditions, and the gas volumes are usually quite high, the size of the pump must grow rapidly, while simultaneously its overall efficiency is dropping rapidly.
2. As the GVF grows, the needs of the recirculation system will increase, along with susceptibility to flashing problems. If trapped liquids are insufficient, then a replenishable external source will be required.

Multiphase Metering

Multiphase Metering is a method to measure the individual phases of oil, gas, and water wile flowing continuously through a flowline. There are numerous methods that have been devised, which are reported in the literature.

To date there have been several commercialized systems. These are:
1. Densitometer based systems by or such as: a. Fluenta; b. Frarno; c. Multi-Fluid International (MFI); d. Kvaerner's CISIRO™; e. Jiskoot's Mixmeter™.
2. Mass Flow Rate based systems by:
   a. WellComp
   b. Accuflow.
3. Volumetric based systems by:
   a. Agar
   b. ISA Controls Ltd. (ISA).

The features of a preferred metering system are:
1. High Rangeability: This refers to the ability of the meter to measure both the liquid rate and the total rate across a broad range. Typically one will have to stretch across a low flow rate on the liquid phase on one well while accommodating a high gas rate on another. This is best done by diversion of the gas through a parallel measuring route. Note that this is not separation; separation deals with getting the gas associated with the oil and water to a minimum value. Under the diversion concept the diverted gas flow needs to be relatively liquid free, while the remaining gas-oil-water flow is sent through a much smaller multiphase meter.
2. Low pressure drop through the metering system. This is needed to allow the meter to measure the productivity of the well without unduly influencing the flow from the well.
3. Good trending results as well as calculation of the running cumulative averages for each phase. This data is used to evaluate the well's reaction to changes (optimization) as well as to know when the test time has been sufficient to give consistent results. Calculation of the cumulative totals for the duration of the test is also needed.
4. Ability to handle various viscosities, salinities, and densities in the test programs.
5. Good communications software that is compatible with the client' systems. (Most customers currently want Modbus protocol; some are asking for Fieldbus capabilities as well.)
6. Low power consumption for the meter and for the computer system.
7. Ability to manage the well testing automatic selection on a high frequency (i.e., daily or hourly) basis. This system should be remote controllable.

Most of the meter manufacturers will include items 3, 5, and 6 in the equipment supplied as part of their "standard" meter. They will also claim to have full capability relative to item 4, but this may be relative to the customer supplying individual data for each well into the metering software that is picked up by the meter's math model when computing the phase rates during the measurement of that respective well. If these variables are unknown, or are dynamically changing during the well test in an unpredictable way, then the Agar meter may come the closest to satisfying the needs. The other meters can also be used, but we will need to supply a sampling device to allow corrections to be used in the calculations (density corrections, salinity corrections, etc.).

WellComp, Agar, and Accuflow normally provide some method that will extend the rangeability of the meter in high gas volume flow conditions. The other meters will need this. The densitometer based systems rely on a system to create, at least temporarily, a fairly homogenous mixture flowing through the meter. By "homogenous" reference is made to the semi-instantaneous cross section of the flow, not a homogenous flow over time. The nature of the multiphase flow is that it is changing with respect to time, so the idea is to measure the changes in the flow cross sections as these pass by the meter's sensors.

Density is measured by the energy absorption of the gamma rays sent into the flow, which can give highly accurate representations if something is known about the constituents which make up the flow (such as the density of the liquid crude, the density of the gas, and the density and composition of the water phase). Sand is generally ignored. The presence of certain atoms which create absorption variances can be calibrated out in the math model to increase the sensitivity and accuracy of the measurements. By measuring at two different points and correlating the results the velocity of similar crosssection results can be obtained, which is used to establish the mass flow rate of the sample.

Water cut is measured using the bulk electrical properties of the flow sample. For the MFI system this measurement is based on microwave energy absorption and phase shift. For Fluenta these measurements are a combination of capacitance and conductance, depending on whether the flow is water continuous or oil continuous.

Both meters rely on a mixing tee placed at the base of the vertically oriented metering section. This method helps to mix initially, but is susceptible to developing bi-directional flow if the rising velocity of the flow is inadequate. Accordingly these meters have a low rangeability, roughly 10:1, that is closely tied to these velocities. In cases where high gas fractions are present, and the meter is sized for these conditions it may encounter serious departures form its stated capabilities when low velocity gas slugs are moving through the meter and the liquids are not "scrubbed out" and can flow back down. One way to extend the rangeability of the metering system is to divert excess gas, and then use a much smaller meter that can maintain the required upward flow rates. This will assist the meter in maintaining a better balance in measuring the three phases that are passed through it.

A decided advantage of this style of meter is its small compact size and the lack of any moving parts. Both of these meters feature very little delta p across the unit, more or less equal to the flow through a tee and straight pipe section.

These meters use a coriolis style meter (Micromotion by Rosemount) placed in the flow stream. It measures the mass flow rate of the liquid mixture directly using the coriolis force generated when the flow traverses two curved sections. The limitation is the presence of a third phase, gas. When gas is present, the density calculation is difficult to make, and if surges of gas is bubble form are present, the high rate of density variation can cause this instrument to stop measuring and reset.

Originally designed to measure water cut in flows of oil and water, it has been adapted to multiphase metering by trying to eliminate the gas phase in such a way that continuous measurements of the total flow, with liquid in one pipe and gas in the other, can be attained. The Accuflow meter comes closest to this ideal, but to do so can require a relatively large piping structure. The WellComp is more compact, uses a high efficiency separator ahead of the meter, and then uses a sampling system in conjunction with the coriolis meter that allows it to handle slightly higher gas fractions through the coriolis meter.

WellComp relies on using a highly developed capacitance probe to determine water cut in the periodic samples taken during the test. This is quite accurate in oil-continuous samples, but lacks precision for the portion of a sample that may be water-continuous. Adjustments are made in the field to calibrate out any of these effects, which can lead to rather long start up periods while the user learns how to calibrate to these local conditions.

Agar's approach relies on an accurate measurement of the total volume entering the meter through a positive displacement meter. The mass flow rate is then taken through to venturi meters place in series which allows the net flow rates of gas and liquid to be determined without relying on density inputs from the user. Agar also uses a high frequency microwave source to measure energy absorption and phase angle change to develop the water cut.

This meter is also velocity sensitive, similar to the Fluenta and MFI meters, however Agar developed a fluidic flow diverter to send excess gas around the meter, greatly extending its range.

The meter has a large range of viscosities it can handle, but the positive displacement meter must be selected for high or low viscosity ranges. The meter is quite susceptible to sand in the flow. There is a vane type positive displacement (PD) meter than can be used to iccrease the resistance to sand, but is much more expensive and the limits are not understood at this time.

THE PRESENT INVENTION

The present invention is based on gas in the incoming flow stream being virtually all free gas, and that a great portion of this gas can be separated and measured, leaving a residual of about 20% or less of gas (by volume) in the liquid stream. This flow stream is then sent into a small pump (preferably about 20–25 HP) which raises the pressure from approximately 55 psi to about 170 psi, sufficient to compress the entrained gas thereby reducing the effective gas volume factor to less than 10 percent. This flow stream is then sent through a mass flow meter and then through a water cut meter. By using these two meters in series, and by supplying a mixed flow to them from the pump, the raw data from the meters can be compared by using a suitable algorithm in a computer to establish the net oil rate and water cut, as well as determine the gas fraction in the liquid flow to an acceptable accuracy.

BRIEF DESCRIPTION OF THE DRAWINGS

FIG. 1.1 shows a diagrammatical view of a typical petroleum production site, where the present invention is adapted for use;

FIG. 1.2 shows a diagrammatical view of a well casing arrangement adapted for use in type typical site shown in FIG. 1.1;

FIG. 1.3 shows a diagrammatical view of a typical producing well adapted for use in the site shown in FIG. 1;

FIG. 2.1 shows a schematic view of multiphase flow patterns;

FIG. 2.2 shows a graphical view of a typical gas volume factor;

FIG. 2.3a and 2.3b show typical twin screw multiphase pumps;

FIGS. 2.4a and 2.4b show graphical views of pressure distribution curves during multiphase flow;

FIG. 2.5 shows sample calculations for sizing a multiphase meter or pump;

FIGS. 3a and 3b show diagrammatical views of preferred embodiments of separation and multiphase systems of the present invention;

DETAILED DESCRIPTION OF PREFERRED EMBODIMENT(S)

Figure 4:
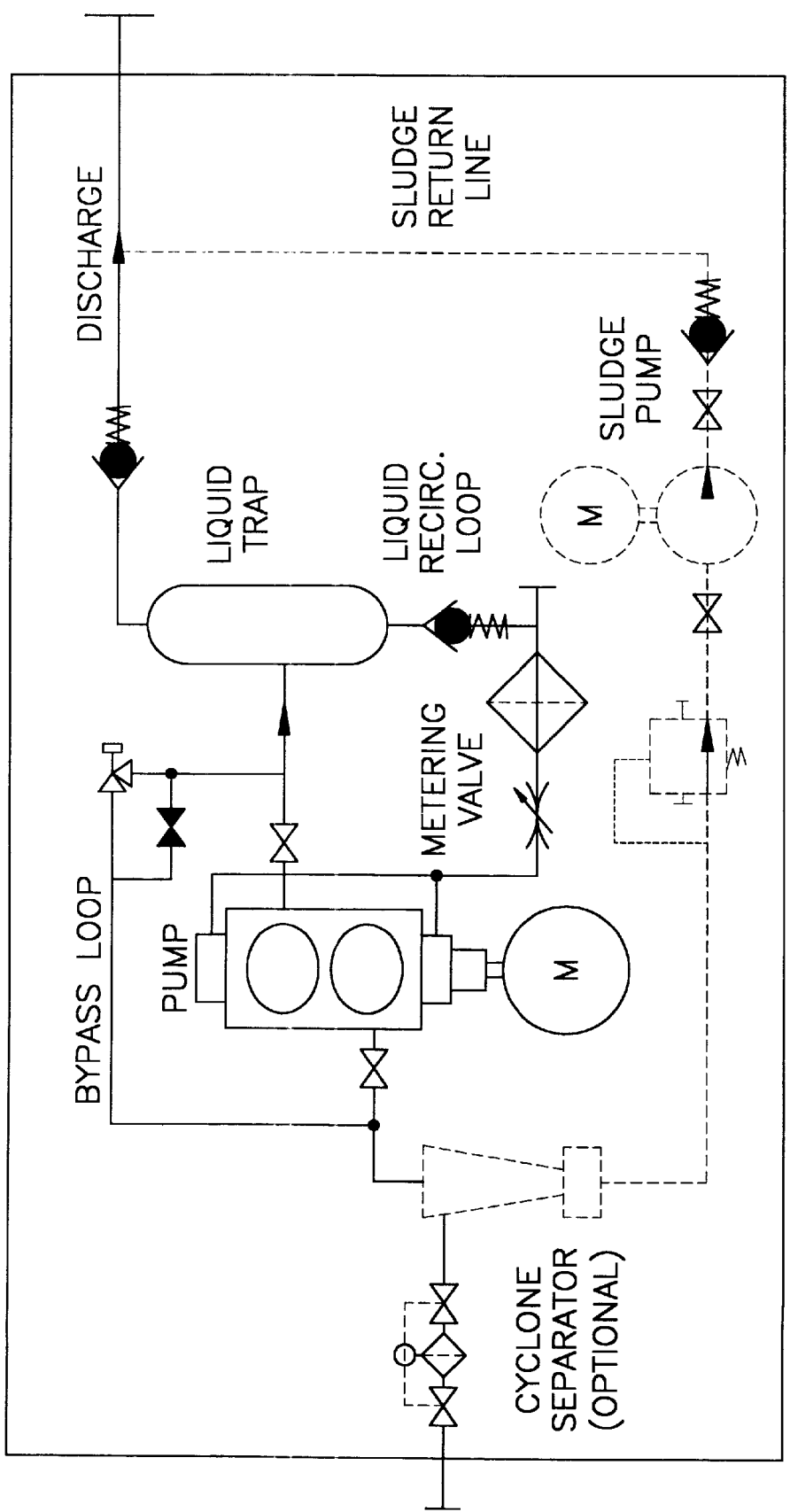
FIG. 4 shows a preferred embodiment of a multiphase pump skid of the present invention.
Figure 5:
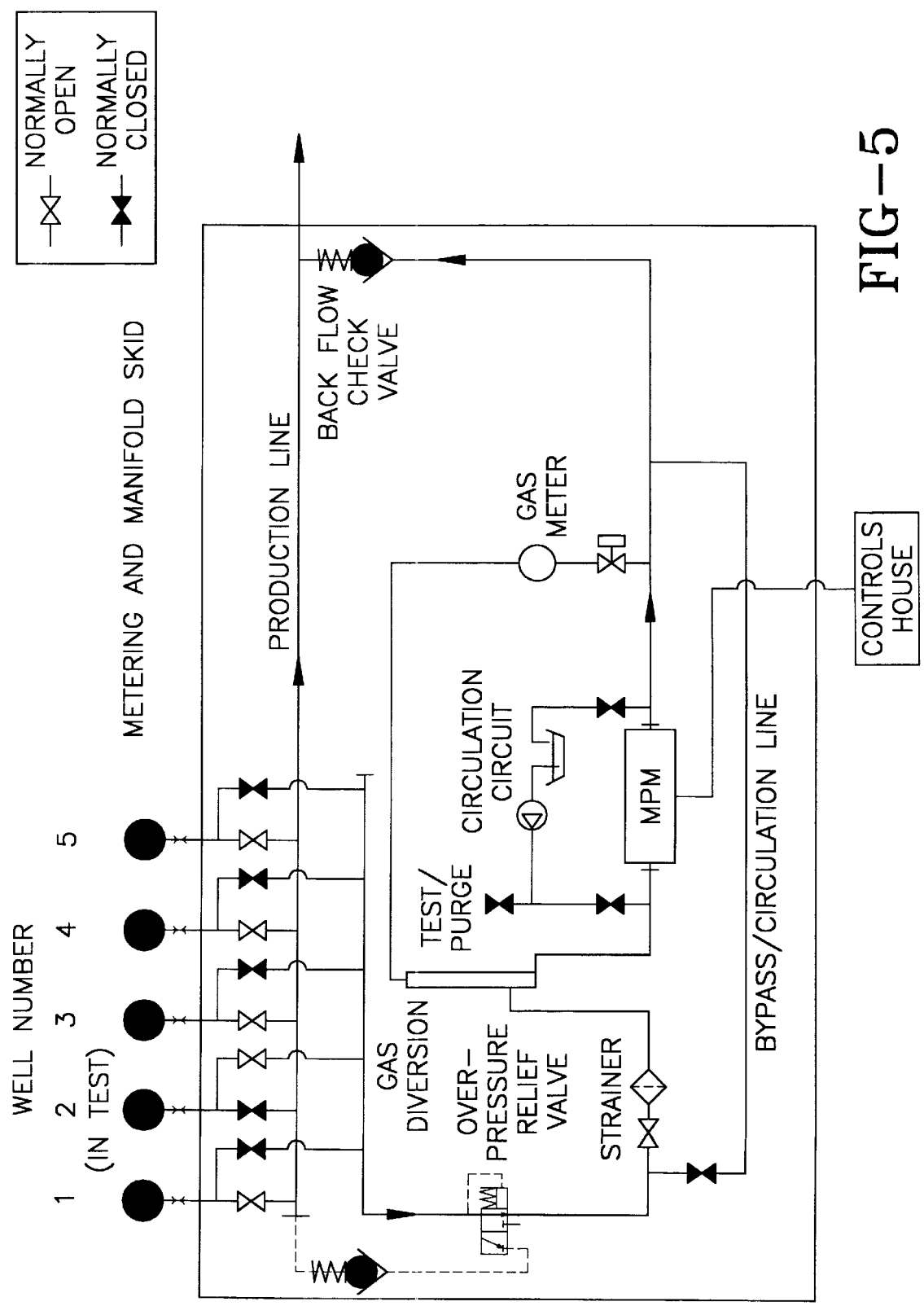
FIG. 5 shows a preferred embodiment of a multiphase metering and manifold skid of the present invention.
Figure 6:
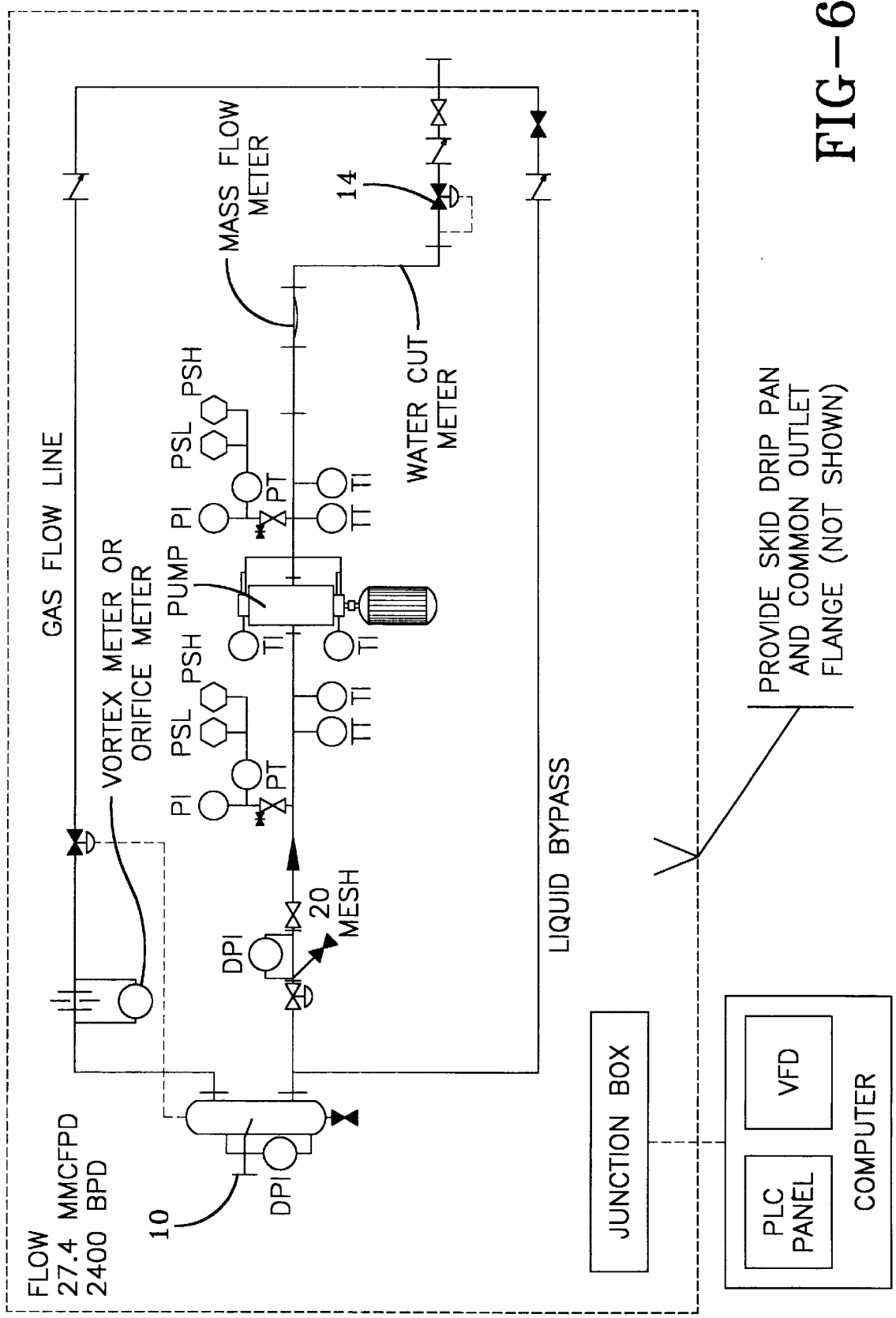
FIG. 6 shows a process and instrument diagram (P&ID) of a preferred embodiment of a multiphase system of the present invention.

Referring now to FIG. 3–9, the present invention is shown in application to different embodiments, and with various features and environments. A multiphase metering and multiphase flow system is described which is based on effecting a preliminary partial gas separation i which the residual gas remaining in the liquid phase is, by volume, about 20% or less, then measuring the residual gas and liquid flow. The separated gas is measured in a parallel flow path as shown in FIG. 6. Multiphase metering may provide well production data on a daily basis and well trending data for real time well and reservoir management.

Referring back to FIG. 3a, an example of a separation system of the present invention is shown. This embodiment of the separation system is comprised of gas lines, oil lines, a water line, a flare or compressor, a water treatment/corrugated plate interceptor (CPI), a crude tank, and a pump. FIG. 3b shows an example of a multiphase system of the present invention. In this example, the multiphase system is comprised of a multiphase meter and a multiphase pump. The multiphase pump may be used to transfer the fluid to a central facility.

FIG. 4 shows an example of a multiphase pump skid of the present invention. The multiphase pump skid of this embodiment is comprised of a bypass loop, a pump, a metering valve, a liquid recirculation loop, a liquid trap, and a discharge line. In addition, the multiphase pump skid optionally includes a cyclone separator, a sludge pump, and a sludge return line.

In FIG. 5, an example of a multiphase metering and manifold skid of the present invention is shown. The skid may be in fluid communication with one or more wells. In this example, the skid is in fluid communication with wells 1, 2, 3, 4, and 5. This embodiment of the skid includes an overpressure relief valve, a strainer, a gas diversion device, an test/purge device, a circulation circuit, a multiphase metering system, a controls house, a bypass/circulation line, a gas meter, a production line, and a back flow check valve.

In FIG. 6, flow enters the system into gas diversion separator 10. Using a vortexing action within gas diversion separator 10, liquids, along with some entrained gas, collect at the base creating a liquid zone and a liquid with free gas above.

Gas moves upward, at very low velocities, allowing any entrained liquid droplets to fall back down. This gas flows up the vertical pipe section and out. This gas stream passes through a back pressure control valve, then is measured such as by a vortex meter or an orifice meter. It then flows through a reverse flow check and a block valve, then can either join back to the liquid line, or be taken off separately.

The liquids stream passes through a reverse flow check, then through a variable speed pump. The pump is controlled by responding to the float valve through a variable frequency drive (VFD) controller. The pump can also circulate during periods of low flow. The pump is set to increase the discharge pressure above the inlet sufficient to reduce the average gas fraction to below 10%, at discharge conditions. The pump also acts as a mixer, homogenizing the flow.

The discharge passes through an optional in-line static mixer, then through a mass flow rate meter, then through a water cut meter (e.g., Phase Dynamics). The flow then passes through valve 14, which reduces the pressure back to the desired line pressure. Optionally, the output of the valve 14 may be recirculated by a liquid bypass line. Measured data and operation diagnostics are received into a remote terminal unit (RTU) panel, and cabled to a computer. The computer may be in communication with a junction box, and it may include a programmable logic control (PLC) panel and a VFD. The analog relationships are compensated for pressure, temperature, and for the calibration constraints of the meter. Using input water and oil densities, the measured water cuts and mass flow rates are corrected for entrained gas. This entrained gas is added to the gas rates and measured with the gas line meter. The output data is the oil, gas, water flow rates, and the water cut, as provided periodically by the computer. These rate values are summed to provide totals for the test.

The gas line may be from the separator as connected back to the discharge line from the meter, or alternatively, the gas line may go elsewhere, and the liquid line to another destination at a different pressure from this metering system. Optionally, a skid drip pan and a common outlet flange may be provided.

Figure 8:
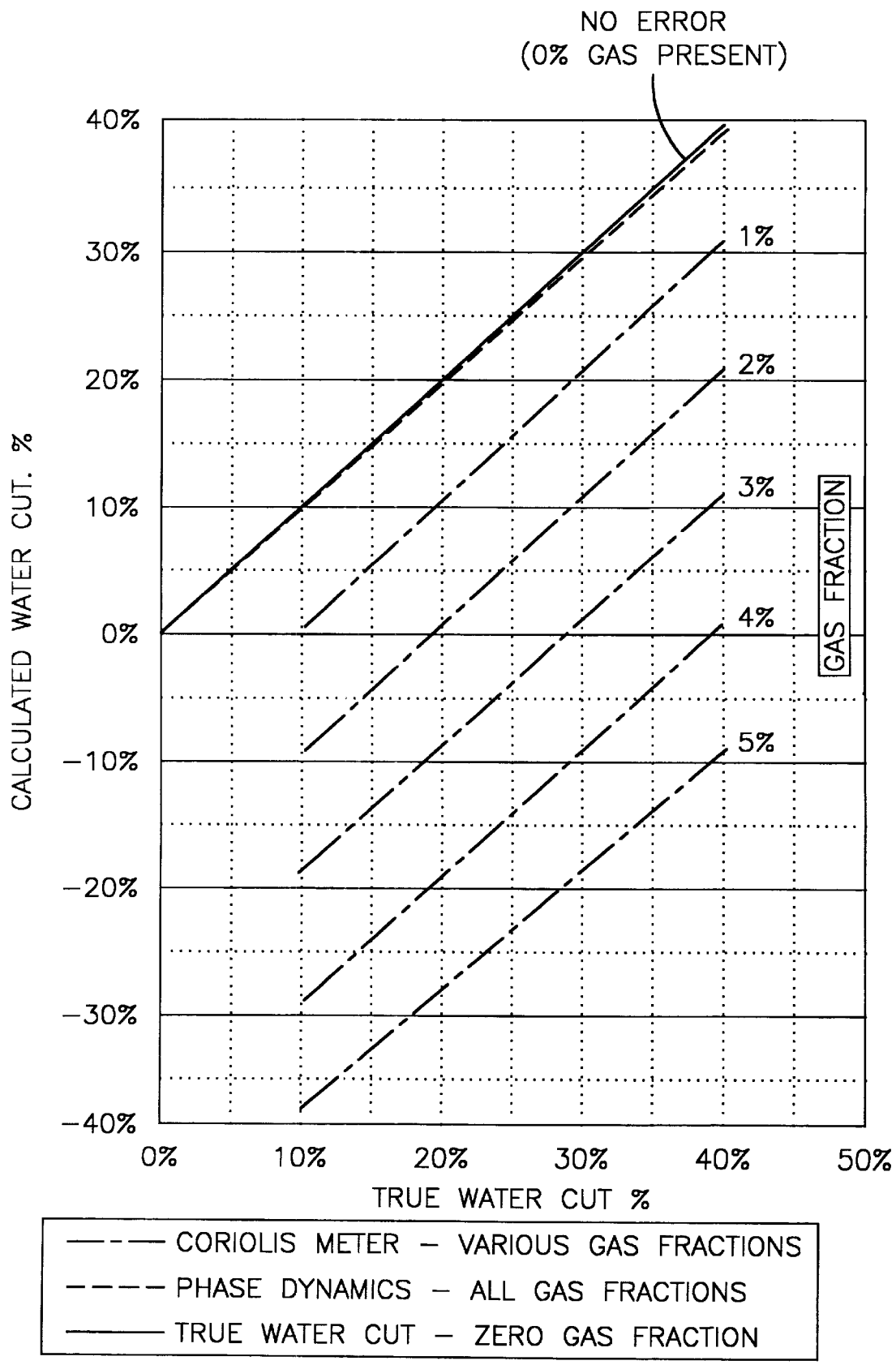
FIG. 8 shows a graph of water cut comparison curves of the present invention.

The water cut compensation curves as shown in FIG. 8 are an example of the relationship between a "perfect" meter and the energy absorption meter when confronted with small gas fraction in the flow. The Phase Dynamics meter line is shown very close to the zero gas friction line indicating there is very little gas dependency in this type of meter. The other lines show what can happen when gas is introduced to the flow and the water cut is a calculated value taken from the results of the coriolis meter. This occurs because the equation uses the density of hydrocarbon as though it is the density of the liquid oil rather than using the real density of the combination of oil and gas. The magnitude of the error is not always as shown in the graph. A new graph should be established for each situation.

Figure 7:
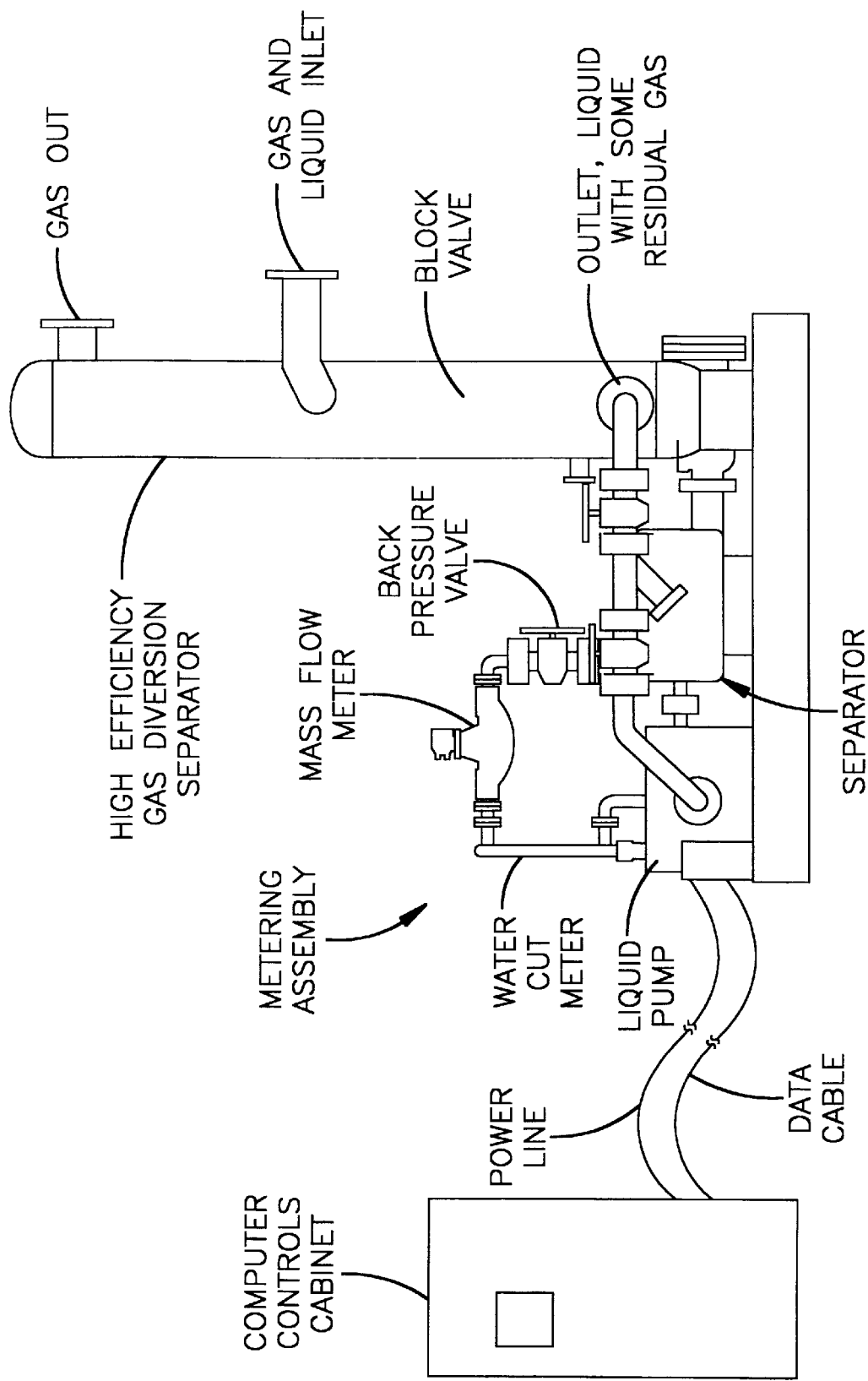
FIG. 7 shows another preferred embodiment of the system of the present invention.
Figure 9:
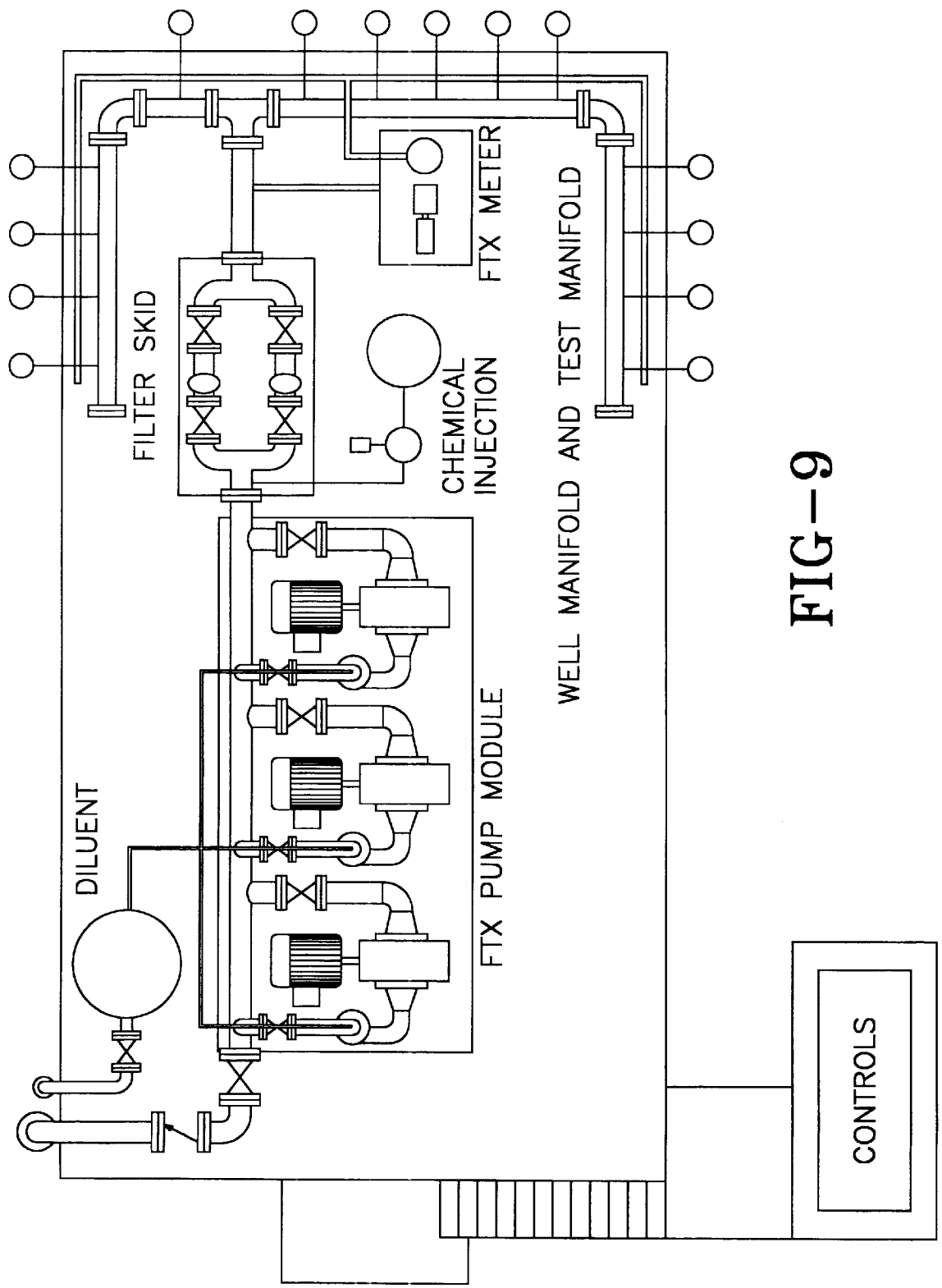
FIG. 9 shows another embodiment of the present invention on a platform arrangement.

FIG. 7 shows a depiction of a system as described in the Example section of the patent specification. In this embodiment, the system is comprised of a computer controls cabinet, a power line, a data cable, a liquid pump, a metering assembly, a gas diversion separator, an outlet for liquid which may contain some residual gas, a block valve, a gas and liquid inlet, and a gas outlet. The metering assembly of this example is comprised of a water cut meter and a mass flow meter. FIG. 9 shows the system of the present invention on an oil platform to test individual wells, then discharge into a common production line from many wells. In this embodiment, three multiphase pumps boost pressure before discharging the oil and gas into a sales line leaving the platform to be processed later on at a central station. This embodiment of the system is comprised of a diluent system, a FTX™ pump module, a filter skid, a chemical injection system, a FTX™ meter, a well manifold, a test manifold, and a controls system. FTX™ is a trademark of Flowtronex International, Inc., a business unit of Rosewood Equipment Corporation.

EXAMPLE

The FTX™ Model 1000

High Range Multiphase Metering System

This a multiphase metering system for measurement of multiphase flow streams that include high gas fractions that may also be combined with medium to high oil viscosities. Water cuts up to 95 percent can be measured with acceptable accuracy and repeatability. Water cuts averaging greater than 95 percent may also be successfully measured, but may require longer testing periods and additional care to input parameters.

General Design

The FTX™ Model 1000 is a multiphase flow measurement system that combines the use of a pump, an energy absorption meter and a density meter in combination with a gas knockout vessel to obtain multiphase flow measurements. It can be used in a wide range of liquid viscosities and gas fractions up to 99+ percent. Depending on the crude type and flow conditions, the knockout vessel may be an existing "standard" two phase separator, or a specially designed vessel for ultra-high efficiency in foamy or heavy crudes [such as a gas liquid compact cyclone separator (GLCC) or a Gas Diversion Separator with Internal Vortex Cluster Tubes (GDX-VC)]. The process requirements for the vessel are simple: It should consistently provide liquids to the pump inlet (located near the bottom) that contain less than 20 percent free gas (by volume) and provide a separate outlet for the gas flow.

The liquids and residual free gas leaving the gas knockout vessel enter the pump inlet and are pressurized sufficiently to result in a low volumetric gas fraction before passing through the water cut meter (Phase Dynamics) and the Mass Flow meter (coriolis type), which are mounted in series. Measurements are taken from both meters to independently arrive at values for water cuts. These values are, in turn, used together to quantify the gas fraction present. This step permits small corrections to be made to the raw meter measurements, resulting in the on-line measurements results of total flow and gas fraction, along with measurement capability of net oil, and water cut to within less than 1 percent error.

These data may be combined with the measurement (optional) of gas flowing from the separator in the gas line to obtain a continuous, three phase flow record of the total production from the well.

The FTX™ system incorporates a PLC as the basis for input data and control commands. The PLC is integrated with the VFD controlling the pump motor speed. Data recorded at the meters (temperatures, pressures, flow rates) are received by the PLC, located in a nonclassified site near the meter. These data, along with key input data are used in an on site computer to calculate the gas fraction in the liquids metering line, and to correct the values reported by the meters. It can also integrate the gas measurements received from the gas meter. These results are stored by the computer and output as continuous (every two-three minutes) flow rate data along with cumulative averages recorded over the previously set test time periods (daily, for example). All data is time stamped, and associated with the operating status reported by the meter sensors to the PLC. This module contains sufficient site storage memory to carry up to an estimated 40 days of flow data. This data can be (automatically) written to a diskette, which is retrievable on a periodic basis (e.g., weekly). Once the memory in the unit is filled, new data is written over the previous data.

A PLC controller is provided to control flow valves, to monitor the pump condition, and to provide for auto-shutdown and switch to bypass. The pumping speed is controlled using a Variable Frequency Drive unit located near the PLC unit. This unit receives its signal from the fluid level indication from the gas knockout vessel, and drives the pump accordingly. It has an infinite turn down ratio to control the pump speed. The pressure developed by the pump in the measurement section is maintained by a back pressure valve, then is reduced prior rejoining the gas measurement leg and entering the main production line.

The FTX™ Model 1000 Metering Assembly: This assembly consists of a screw pump, designed to pump up to 1200 barrels per day (BPD) of either a liquid, or a liquid with gas mixture, allowing a pressure increase (nominally 250 psi), and requiring a 15–20 HP inverter duty electric motor. The pumping system creates a pressurized liquid/gas mixture in the metering section that is 2–3.5 times greater than the inlet pressure conditions and provides ample flow energy to travel through the meters, maintaining pressures well above the inlet conditions. This allows optimal meter size selection for best precision in the flow ranges anticipated, as minimizing pressure drops through these meters is not a primary concern. After metering the flow is well above the inlet pressure, and is then reduced to recombine with the gas leg pressure. This means that even under maximum flow and surge conditions, pressure drops through this meter are governed by the gas leg flow conditions and will be nominal, on the order of 1.5–3 psi.

These liquid leg meters include a coriolis effect mass flow meter, and a Phase Dynamics, meter to determine the water cut. The function of the coriolis effect meter is to provide the flow rate of the mixture and the function of the Phase Dynamics meter is to measure the water cut. A separate water cut is also be determined independently using the coriolis effect meter and used indirectly to estimate the quantity of gas present. A pressure modulated control valve then drops this pressure before joining the liquid flow to the gas flowing from the gas leg.

1. Diagnostics:

Diagnostic information reporting the condition of the metering system is provided by the raw data received at the PLC when compared to the range expected in order to check the operation condition of the transmitters. A comparison check is also made of the results from the coriolis meter against the rotating speed of the pump to verify that the expected relationship between overall volume and measured mass flow is consistent. Comparison between the gas flow data and the water cut comparative data also provides a diagnostic check on the operating condition in the gas diversion separator, and the flow conditions in the metering leg. Finally, a delta p measurement across the gas meter in the gas metering leg provides a check on the quality of the gas flowing in that side of the meter, as well as a check on the operation of the vortex shedding meter. Out-of-specification warnings are issued by the software program and recorded with the test data to alert the user as to any suspect condition.

2. Bypass Operations:

The entire unit can be isolated for maintenance purposes or when ever a shutdown occurs due to loss of power. An alarm is shown on the data control screen whenever the unit is in the bypass configuration.

3. The Control and Data Acquisition System:

This is composed of three elements: The VFD unit, which controls the speed of the pump, the PLC unit, which has the primary data inputs, operates the valves, and controls power to the pump, operates the starter, and monitors and reports the operation of the system, and the Data Acquisition Computer, which, using its proprietary software package, receives the data outputs from the meters, and calculates the gas fraction, makes the corrections, manages the data, and manages the outputs and communications to the customer's data system, and to local (e.g.; portable computer, diskette) interfaces. These three elements are designed to be housed away from a classified area, or housed in a manner that will allow them to be used and interacted with personnel who are working near the size.

4. Physical Dimensions/Specifications:

The Metering and Separator skid assembly is constructed as a unit, approximately 6–10 feet long by 4–6 feet wide, (depending on the gas volumes and the separator system used with the metering system).

All equipment located on the metering skid is suitable for operation in a Class I, Div. II area. The PLC, VFD, and Data Acquisition Computer are not normally supplied as explosion proof rated equipment, and should be housed away from a classified area, or otherwise suitably housed or shielded.

5. Power Requirements:

The unit requires electrical power for the 20 HP pump motor and VFD unit. Another 300 watts will be required to operate the PLC and Data Acquisition Computer. The valve operators selected are based on using natural gas as the energy source (bypass line and back pressure valve on the metering line).

The preceding description of the present invention is one of a preferred embodiment(s) and is not intended nor required to be a description of all manners in which the unique features and aspects of the present invention may be incorporated. It is likely that those skilled in the art will, upon reading this disclosure, find variations and modifications in the implementation of the invention, and such are considered to be captured by the following claims.

The preceding description is considered merely to be an example of one implementation of the present invention of which many implementations are readily available from the description set forth herein.

What is claimed is:

1. A multiphase metering method for a multiphase flow stream including gas, water, and oil and having a gas volume and a pressure, comprising the steps of:

reducing the gas volume in the multiphase flow stream;

determining a first water cut value of the multiphase flow stream;

determining a second water cut value of the multiphase flow stream;

comparing the first water cut value to the second water cut value to estimate the gas volume present in the multiphase flow stream; and computing at least one parameter of the multiphase flow stream considering the estimated gas volume in the multiphase flow stream.

2. The method of claim 1, wherein the step of reducing the gas volume includes the step of using a vortexing action.

3. The method of claim 1, wherein the step of reducing the gas volume further includes the step of raising a pressure.

4. The method of claim 1, wherein the step of reducing the gas volume further includes the step of providing a gas diversion separator to reduce the gas volume.

5. The method of claim 4, wherein the step of providing the gas diversion separator further includes the step of using a vortexing action to reduce the gas volume.

6. The method of claim 1, wherein the step of reducing the gas volume in the multiphase flow stream further includes the step of raising a pressure of the multiphase flow system by passing the multiphase flow stream through a pressurizing device, thereby reducing the gas volume.

7. The method of claim 6, wherein the step of raising the pressure further includes the step of pumping the multiphase flow stream to raise the pressure.

8. The method of claim 7, wherein the step of reducing the gas volume further includes the step of passing the multiphase flow stream through the gas diversion separator and then through a pump.

9. The method of claim 8, wherein the step of reducing the gas volume further includes the steps of:

reducing the gas volume to less than about 20% by using a vortexing action; and further reducing the gas volume to less than about 10% by raising the pressure.

10. The method of claim 1, further comprising the steps of:
   providing a mass flow meter to use in the step of determining the first water cut value; and
   providing a water cut meter to use in the step of determining the second water cut value.

11. The method of claim 1, wherein the step of computing the at least one parameter of the multiphase flow stream further includes the step of computing the at least one parameter from the group consisting of water volume, oil volume, liquid volume, mass flow rate, oil flow rate, gas flow rate, water flow rate, water cut, and gas fraction.

12. A system for multiphase metering of a multiphase flow stream including gas, water, and oil, comprising:
   a gas diversion separator reducing a gas volume in the multiphase flow stream;
   a mass flow meter in fluid communication with said gas diversion separator, and mass flow meter determining a first water cut value;
   a water cut meter connected in series with said mass flow meter, the water cut meter determining a second water cut value; and
   a computing device in communication with the mass flow meter and the water cut meter, the computing device comparing the first water cut value to the second water cut value to estimate the gas volume present in the multiphase flow stream, the computing device further computing at least one parameter of the multiphase flow stream considering the estimated gas volume in the multiphase flow stream.

13. The system of claim 12, wherein the gas diversion separator uses a vortexing action to reduce the gas volume of the multiphase flow stream.

14. The system of claim 12, wherein the gas diversion separator reduces the gas volume to less than about 20%.

15. The system of claim 12, further comprising a pump in fluid communication with the gas diversion separator and the mass flow meter to raise a pressure of the multiphase flow stream.

16. The system of claim 15, wherein the pump reduces the gas volume to less than about 10%.

17. The system of claim 12, wherein the mass flow meter is a coriolis meter.

18. The system of claim 12, wherein the at least one parameter of the multiphase flow stream is selected from the group consisting of water volume, oil volume, liquid volume, mass flow rate, oil flow rate, gas flow rate, water flow rate, water cut, and gas fraction.

* * * * *

UNITED STATES PATENT AND TRADEMARK OFFICE
CERTIFICATE OF CORRECTION

PATENT NO. : 6,234,030 B1
DATED : May 22, 2001
INVENTOR(S) : Bryan V. Butler

It is certified that error appears in the above-identified patent and that said Letters Patent is hereby corrected as shown below:

Column 1,
Line 66, please delete the word "is" and replace it with -- it --.

Column 4,
Line 62, please delete the word "is" and replace it with -- it --.

Column 5,
Line 47, please delete the word "survey" and replace it with -- surety --.
Line 48, please delete the word "when" and replace it with -- what --.

Column 7,
Line 24, please delete the word "tread" and replace it with -- thread --.

Column 8,
Line 38, please delete the word "warm" and replace it with -- warn --.

Column 12,
Line 17, please delete the letter "i" and replace it with -- in --.

Column 13,
Line 29, please delete the word "friction" and replace it with -- fraction --.

Column 15,
Line 62, please delete the word "size" and replace it with -- site --.

Column 16,
Line 52, please delete the word "system" and replace it with -- stream --.

UNITED STATES PATENT AND TRADEMARK OFFICE
CERTIFICATE OF CORRECTION

PATENT NO. : 6,234,030 B1
DATED : May 22, 2001
INVENTOR(S) : Bryan V. Butler

It is certified that error appears in the above-identified patent and that said Letters Patent is hereby corrected as shown below:

<u>Column 17,</u>
Line 18, please delete the word "and" and replace it with -- said --.

Signed and Sealed this

Eighth Day of January, 2002

*Attest:*

*Attesting Officer*

JAMES E. ROGAN
*Director of the United States Patent and Trademark Office*